United States Patent
Breunig et al.

(10) Patent No.: US 11,466,290 B2
(45) Date of Patent: Oct. 11, 2022

(54) SYSTEMS AND METHODS FOR IN VIVO DUAL RECOMBINASE-MEDIATED CASSETTE EXCHANGE (DRMCE) AND DISEASE MODELS THEREOF

(71) Applicant: CEDARS-SINAI MEDICAL CENTER, Los Angeles, CA (US)

(72) Inventors: Joshua Breunig, Los Angeles, CA (US); Moise Danielpour, Los Angeles, CA (US); Gi Bum Kim, North Hollywood, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 308 days.

(21) Appl. No.: 16/071,407

(22) PCT Filed: Dec. 30, 2016

(86) PCT No.: PCT/US2016/069442
§ 371 (c)(1),
(2) Date: Jul. 19, 2018

(87) PCT Pub. No.: WO2017/131926
PCT Pub. Date: Aug. 3, 2017

(65) Prior Publication Data
US 2019/0390222 A1 Dec. 26, 2019

Related U.S. Application Data

(60) Provisional application No. 62/287,197, filed on Jan. 26, 2016.

(51) Int. Cl.
| | |
|---|---|
| *C12N 15/85* | (2006.01) |
| *A01K 67/027* | (2006.01) |
| *A61K 48/00* | (2006.01) |
| *A61K 49/00* | (2006.01) |
| *C12N 9/22* | (2006.01) |
| *C12N 15/11* | (2006.01) |

(52) U.S. Cl.
CPC ...... *C12N 15/8509* (2013.01); *A01K 67/0275* (2013.01); *A61K 48/0066* (2013.01); *A61K 49/0008* (2013.01); *C12N 9/22* (2013.01); *C12N 15/11* (2013.01); *A01K 2217/07* (2013.01); *A01K 2227/105* (2013.01); *A01K 2267/0331* (2013.01); *C12N 2015/8572* (2013.01); *C12N 2310/20* (2017.05); *C12N 2800/80* (2013.01); *C12N 2830/50* (2013.01)

(58) Field of Classification Search
CPC ...... C12N 15/8509; C12N 9/22; C12N 15/11; C12N 2310/20; C12N 2015/8572; C12N 2800/80; C12N 2830/50; C12N 2015/8527; C12N 2800/30; A01K 67/0275; A01K 2217/07; A01K 2227/105; A61K 48/0066; A61K 49/0008
See application file for complete search history.

(56) References Cited

U.S. PATENT DOCUMENTS

| | | | |
|---|---|---|---|
| 2003/0084468 A1* | 5/2003 | Economides | A01K 67/0275 800/18 |
| 2003/0228295 A1 | 12/2003 | Svendsen | |
| 2010/0077495 A1* | 3/2010 | Davis | C12N 15/1136 800/14 |
| 2010/0240133 A1 | 9/2010 | Brivanlou et al. | |
| 2012/0107938 A1* | 5/2012 | Lopez-Rios | C12N 15/8509 435/462 |
| 2013/0115692 A1* | 5/2013 | Trono | C12N 7/00 435/320.1 |
| 2015/0044187 A1 | 2/2015 | Visel et al. | |
| 2016/0060651 A1 | 3/2016 | Alphey | |
| 2017/0137781 A1 | 5/2017 | Qiang et al. | |
| 2017/0216456 A1 | 8/2017 | Alexander et al. | |
| 2017/0274048 A1 | 9/2017 | Neves et al. | |
| 2018/0021383 A1 | 1/2018 | George et al. | |
| 2021/0024955 A1 | 1/2021 | Svendsen et al. | |

FOREIGN PATENT DOCUMENTS

| | | |
|---|---|---|
| AU | 2016389495 A1 | 8/2018 |
| AU | 2019236288 A1 | 9/2020 |
| CA | 3012042 A1 | 8/2017 |
| CA | 3092284 A1 | 9/2019 |
| CN | 108884472 A | 11/2018 |
| CN | 111867617 A | 10/2020 |
| EP | 2977449 A1 | 1/2016 |
| EP | 3408396 A1 | 12/2018 |
| EP | 3765058 A1 | 1/2021 |
| HK | 40001420 | 2/2020 |

(Continued)

OTHER PUBLICATIONS

Osterwalder, Marco. "Genome-wide identification of Hand2 target regions in mouse embryos using dRMCE, a new genetic tool." (2012). (Year: 2012).*
Chen et al. "Engineering Human Stem Cell Lines with Inducible Gene Knockout using CRISPR/Cas9" Cell Stem Cell. Aug. 6, 2015;17(2):233-44. (Year: 2015).*
International Search Report and Written Opinion for PCT/US2016/069442 dated Jun. 2, 2017, 13 pages.
Akhtar et al., A Transposon-Mediated System for Flexible Control of Transgene Expression in Stem and Progenitor-Derived Lineages, Stem Cell Reports, 2015, vol. 4, pp. 323-331.
Zeller et al., Gene Cutting and Pasting Just Got a Whole Lot Faster, Nature Methods, 2010, vol. 7(11), p. 861.

(Continued)

*Primary Examiner* — Titilayo Moloye
(74) *Attorney, Agent, or Firm* — Nixon Peabody LLP; Linda B. Huber

(57) ABSTRACT

Described herein are donor vectors and systems for use in in vivo dual recombinase-mediated cassette exchange. Also described are animal models for consistent, rigorous, and facile investigation of transgene expression. Further described are methods of screening for therapeutic drugs using these animal models, and methods of treatment.

12 Claims, 25 Drawing Sheets
Specification includes a Sequence Listing.

(56) References Cited

FOREIGN PATENT DOCUMENTS

| | | | |
|---|---|---|---|
| JP | 2019511243 A | 4/2019 | |
| JP | 2021-518365 A | 8/2021 | |
| KR | 20180101535 A | 9/2018 | |
| KR | 20200132957 A | 11/2020 | |
| WO | 2011001247 A2 | 1/2011 | |
| WO | 2014127289 A1 | 8/2014 | |
| WO | 2014204724 A1 | 12/2014 | |
| WO | 2017079673 A1 | 5/2017 | |
| WO | 2017131926 A1 | 8/2017 | |
| WO | 20190178550 A1 | 9/2019 | |
| WO | 2020257205 A1 | 12/2020 | |

OTHER PUBLICATIONS

International Search Report and Written Opinion for PCT/US2019/022595 dated Jun. 10, 2019, 19 pages.

Guan et al., Establishing isogenic inducible cell lines using founder reporter lines and recombinase-mediated cassette exchange, Biotechniques, 2013, vol. 55(5), pp. 233-242.

Cobellis et al., Tagging Genes with Cassette-Exchange Sites, Nucleic Acids Research, 2005, vol. 33(4), pp. 1-7.

Galli et al., Distinct Roles of Hand2 in Initiating Polarity and Posterior Shh Expression during the Onset of Mouse Limb Bud Development, PLoS Genetics, 2010, vol. 6(4), pp. 1-14.

Hohenstein et al., High-Efficiency Rosa26 Knock-in Vector Construction for Cre-Regulated Overexpression and RNAi, PathoGenetics, 2008, vol. 1(1), pp. 1-10.

Lauth et al., Stable and Efficient Cassette Exchange Under Non-Selectable Conditions by Combined Use of Two Site-Specific Recombinases, Nucleic Acids Research 2002, vol. 30(21).

Lopez-Rios et al., GLI3 Constrains Digit Number by Controlling Both Progenitor Proliferation and BMP-Dependent Exit to Chondrogenesis, Developmental Cell, 2012, pp. 1-70.

Osterwalder et al., Dual RMCE for Efficient Re-Engineering of Mouse Mutant Alleles, Nature Methods, 2010, pp. 1-12.

Osterwalder et al., Next Generation Engineering of Conditional Mouse Alleles with loxP and FRT sites by Dual RMCE, Protocol Exchange, 2010, Abstract Only.

Osterwalder et al., Genome-Wide Identification of Hand2 Target Regions in Mouse Embryos using dRMCE, A New Genetic Tool, Basel, 2012, pp. 1-203.

Breunig et al., Platform presentation, SNO Meeting, 2013, 16 pages.

Breunig, et al., Ets Factors Regulate Neural Stem Cell Depletion and Gliogenesis in Ras Pathway Glioma, Cell Reports, Jul. 14, 2015, 12:258-271.

International Search Report and Written Opinion for PCT/US2020/037946 dated Sep. 16, 2020, 14 pages.

Zhang et al., Human Neural Stem Cells with GDNF Site-Specific Integration at AAVS1 by using AAV Vectors Retained Their Stemness, Neurochem Res, 2018, vol. 43(4), pp. 930-937.

Karimova et al., Discovery of Nigri/nox and Panto/pox site-specific recombinase systems facilities advanced genome engineering, Sci Rep, 2016, vol. 6(30130), pp. 1-13.

De Groot et al., In vivo induction of glial cell proliferation and axonal outgrowth and myelination by brain-derived neurotrophic factor, Mol Endocrinol, 2006, vol. 20(11), pp. 2987-2998.

Sullivan et al., Neurotrophic factor therapy for Parkinson's disease: past, present and future, Neural Regen Res, 2016, vol. 11(2), pp. 205-207.

EP 19768063.0 European Extended Search Report dated Nov. 24, 2021, 10 pages.

Abbasi et al., Inducible Expression of GDNF in Transplanted PSC-Derived Neural Progenitor Cells, Stem Cell Reports, 2018, vol. 10(6), pp. 1696-1704.

Suzuki et al., GDNF Secreting Human Neural Progenitor Cells Protect Dying Motor Neurons, but Not Their Projection to Muscle, in a Rat Model of Familial ALS, PLOS ONE, 2007, vol. 2(8).

\* cited by examiner

F

C

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
gcaacgtgct ggttattgtg c                                    21

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
ctcaatccag cggaccttcc                                      20

-continued

<210> SEQ ID NO 3
<211> LENGTH: 21
<212> TYPE: DNA
<213> ORGANISM: Artificial Sequence
<220> FEATURE:
<223> OTHER INFORMATION: synthetic construct

<400> SEQUENCE: 3
agcaaagacc ccaacgagaa g                                           21

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
tgtctggatc cccatcaagc                                             20

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
atgccctggc tcacaaatac                                             20

<210> SEQ ID NO 6
<211> LENGTH: 18
<212> TYPE: DNA
<213> ORGANISM: Artificial Sequence
<220> FEATURE:
<223> OTHER INFORMATION: synthetic construct

<400> SEQUENCE: 6
acacaggcat agagtgtc                                               18

<210> SEQ ID NO 7
<211> LENGTH: 22
<212> TYPE: DNA
<213> ORGANISM: Artificial Sequence
<220> FEATURE:
<223> OTHER INFORMATION: synthetic construct

<400> SEQUENCE: 7
gatgacggcc atgttgttgt cc                                          22

<210> SEQ ID NO 8
<211> LENGTH: 23
<212> TYPE: DNA
<213> ORGANISM: Artificial Sequence
<220> FEATURE:
<223> OTHER INFORMATION: synthetic construct

<400> SEQUENCE: 8
tttaacagag agaagttcgt ggc                                         23

<210> SEQ ID NO 9
<211> LENGTH: 21
<212> TYPE: DNA
<213> ORGANISM: Artificial Sequence
<220> FEATURE:
<223> OTHER INFORMATION: synthetic construct

<400> SEQUENCE: 9
ggagcgggag aaatggatat g                                             21

<210> SEQ ID NO 10
<211> LENGTH: 23
<212> TYPE: DNA
<213> ORGANISM: Artificial Sequence
<220> FEATURE:
<223> OTHER INFORMATION: synthetic construct

<400> SEQUENCE: 10
cgaaaggccc ggagatgagg aag                                           23

<210> SEQ ID NO 11
<211> LENGTH: 20
<212> TYPE: DNA
<213> ORGANISM: Artificial Sequence
<220> FEATURE:
<223> OTHER INFORMATION: synthetic construct

<400> SEQUENCE: 11
tgatcgcgct tctcgttggg                                               20

<210> SEQ ID NO 12
<211> LENGTH: 8
<212> TYPE: DNA
<213> ORGANISM: Artificial Sequence
<220> FEATURE:
<223> OTHER INFORMATION: synthetic construct

<400> SEQUENCE: 12 gcatacat                                                            8

<210> SEQ ID NO 13
<211> LENGTH: 34
<212> TYPE: DNA
<213> ORGANISM: Artificial Sequence
<220> FEATURE:
<223> OTHER INFORMATION: synthetic construct

<400> SEQUENCE: 13
gaagttccta ttctctagaa agtataggaa cttc                               34

<210> SEQ ID NO 14
<211> LENGTH: 9
<212> TYPE: DNA
<213> ORGANISM: Artificial Sequence
<220> FEATURE:
<223> OTHER INFORMATION: synthetic construct

<400> SEQUENCE: 14 atagtatgc                                                           9

<210> SEQ ID NO 15
<211> LENGTH: 30
<212> TYPE: DNA
<213> ORGANISM: Artificial Sequence
<220> FEATURE:
<223> OTHER INFORMATION: synthetic construct

<400> SEQUENCE: 15
aactccctcg atgtggcggc tcatctgccc                                    30

<210> SEQ ID NO 16
<211> LENGTH: 31

```
<212> TYPE: DNA
<213> ORGANISM: Artificial Sequence
<220> FEATURE:
<223> OTHER INFORMATION: synthetic construct

<400> SEQUENCE: 16
aactccctcg aatgtggcgg ctcatctgcc c                                      31

<210> SEQ ID NO 17
<211> LENGTH: 29
<212> TYPE: DNA
<213> ORGANISM: Artificial Sequence
<220> FEATURE:
<223> OTHER INFORMATION: synthetic construct

<400> SEQUENCE: 17
tctcctggct cagagggagc tcgaggctg                                         29

<210> SEQ ID NO 18
<211> LENGTH: 22
<212> TYPE: DNA
<213> ORGANISM: Artificial Sequence
<220> FEATURE:
<223> OTHER INFORMATION: synthetic construct

<400> SEQUENCE: 18
tctcagaggg agctcgaggc tg                                                22

<210> SEQ ID NO 19
<211> LENGTH: 34
<212> TYPE: DNA
<213> ORGANISM: Artificial Sequence
<220> FEATURE:
<223> OTHER INFORMATION: synthetic construct

<400> SEQUENCE: 19
ataacttcgt atagcataca ttatacgaag ttat                                   34

<210> SEQ ID NO 20
<211> LENGTH: 34
<212> TYPE: DNA
<213> ORGANISM: Artificial Sequence
<220> FEATURE:
<223> OTHER INFORMATION: synthetic construct

<400> SEQUENCE: 20
ataacttcgt ataatgtatg ctatacgaag ttat                                   34
```

SYSTEMS AND METHODS FOR IN VIVO DUAL RECOMBINASE-MEDIATED CASSETTE EXCHANGE (DRMCE) AND DISEASE MODELS THEREOF

CROSS-REFERENCE TO RELATED APPLICATIONS

This application is a National Phase of International Application No. PCT/US2016/069442, filed Dec. 30, 2016, which designated the U.S. and that International Application was published under PCT Article 21(2) in English. This application claims priority under 35 U.S.C. § 119(e) to U.S. Provisional Application No. 62/287,197, filed Jan. 26, 2016, the contents of which are herein incorporated by reference in their entirety.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Genetically engineered mouse models (GEMMs), especially those that enable conditional somatic mosaicism, have been the gold standard for conducting reverse genetics in a temporal- and tissue-specific manner. Given that GEMM generation is a laborious process, many alternative non-GEMM models, such as electroporation-mediated (EP) and viral gene deliveries are increasingly employed as a more rapid means of creating somatic mosaics, such as modeling tumors. Both techniques can virtually target anywhere in the body. In addition to the tetracycline-regulated system (TRE) and shRNAs, EP has recently incorporated transposon, such as piggyBac (PB-EP), enabling stable and inducible transgenesis and tumor generation in vivo.

Despite offering speed and flexibility, PB-EP and viral methods have many pitfalls. Viral vectors have limited payloads, incite immune responses, and require complex preparation expertise, and both PB-EP and viral delivery suffer from their unpredictable genomic integration patterns, subsequent insertional mutagenesis, and epigenetic transgene silencing. Most importantly for interrogation of gain-of-function (GOF) mutations, both non-GEMM techniques result in clonal genotypic/phenotypic variability, often caused by transgene copy number variation (CNV) or chromosomal-positional variability, whereas GEMMs ensure constant gene dosage and zygosity quantified during mouse engineering. Therefore, non-GEMM-based evaluation of GOF protein functions is often confounded by such supra-physiological phenomena as overexpression artifacts, unintended cytotoxicity, and transcriptional squelching.

Accordingly, there remains an unmet need in the art for these types of animal models and tools for research applications, disease modeling, drug screening, and therapies.

BRIEF DESCRIPTION OF THE FIGURES

Exemplary embodiments are illustrated in referenced figures. It is intended that the embodiments and figures disclosed herein are to be considered illustrative rather than restrictive.

FIGS. 1A-1F show that dRMCE in heterozygous mTmG generates three recombinant lineages in vivo and in vitro in accordance with various embodiments of the present invention. FIG. 1a) Flp-Cre expression vector catalyzes either Cre-mediated excision or dRMCE on Rosa26m$^{TmG}$ allele in the presence a dRMCE donor vector, resulting in two distinct recombinant products. FIG. 1b) Nucleofection of heterozygous Rosa26$^{WT/mTmG}$ mNSCs result in three possible lineages: tdTomato+, EGFP+, and TagBFP2+. FIG. 1c) Live imaging of representative cells with non-overlapping fluorescent colors. Scale bars: 100 µm. FIG. 1d) Standard postnatal electroporation protocol targeting the VZ/SVZ cells in P2 heterozygous Rosa26$^{WT/mTmG}$ pups with DNA mixture of a Flp-Cre expression vector and a donor plasmid. FIG. 1e) Postnatal EP recapitulates in vitro nucleofection experiment and yields olfactory neurogenesis and striatum gliogenesis by 2 weeks post-EP. Scale bars: 100 µm. FIG. 1f) DNA mixtures of different concentration of recombinase and donor plasmids result in various efficiencies of both MADR and Cre-excision recombination reactions in vivo, illustrating that the in vivo dRMCE reaction efficiency can be modulated.

FIGS. 2a-2b) Postnatal EP in homozygous Rosa26m$^{TmG}$ P2 pups with Hras$^{G12V}$ oncogene produces two different tumor types (Blue-only Rosa26$^{HrasG12V\times2}$ and blue-and-green Rosa26$^{HrasG12V\times1}$). FIG. 2c) Representative tumor formation in homozygous mTmG 3 months post-EP. Blue-only Rosa26$^{HrasG12V\times2}$ cells occupy a larger section of the tumor than blue-and-green Rosa26$^{HrasG12V\times1}$. Scale bars: 2 mm. FIGS. 2d-2e, 2j) Donor construct for miR-E shRNAs against Nf1, Pten, and Trp53 tied to TagBFP2 reporter, and representative 6-month-old mouse sagittal section showing that TagBFP2+ cells are Pdgfra+. Scale bars: 200 µm and 20 µm. FIGS. 2f-2g) Two donor constructs encoding two combinations of pediatric glioma mutations and subsequent hyperplasias in heterozygous Rosa26$^{WT/mTmG}$ in P50 brains. Scale bars: 2 mm. FIGS. 2h-2i) Donor construct for miR-E shRNAs against Nf1, Pten, and Trp53 results in approximately 80% mRNA level knockdown efficiency as measured by qPCR.

FIG. 3a) Schematic of recombinase-expressing plasmids employed. FIG. 3b) FACS analysis indicates the approximate dRMCE efficiency in neural stem cells, and no obvious difference between Flp-2A-Cre and Flp-IRES-Cre in their catalytic efficiencies. FIG. 3c) Sorted cells express Hras$^{G12V}$ but not tdTomato or EGFP. Scale bar: 50 µm. FIG. 3d) Western blot indicating normal transgene production from non-clonal aggregate cells and lack thereof in FACS negative population. Removal of tdTomato expression is also observed.

FIG. 4a) dRMCE-compatible TRE plasmid FIG. 4b) Heterozygous mTmG mNSCs are nucleofected with plasmid in FIG. 4a), treated with puromycin, and turned into a colorless population. Scale bars: 10 µm FIG. 4c) Induction of EGFP expression in the cell line that constitutively express rtTA-V10-AU1. Scale bars: 50 µm FIG. 4d) TRE cell line that express Dll1 upon doxycycline treatment with population-wide uniform expression distribution. Scale bars: 20 µm. FIGS. 4e-4g) After creating 4 distinct dRMCE donor plasmids, all carrying rtTA-V10-AU1 and each carrying SM-FP-Flag, -Myc, -HA, and -V5, the heterozygous mTmG mNSCs carrying a single Rosa26 allele were nucleofected with all four aforementioned SM-FP variant plasmids, treated with puromycin, and treated with doxycycline. Induction of SM-FP probes shows that there is no overlap of SM-FP signal, demonstrating that each cell has exactly one SM-FP variant under Rosa26 CAG promoter control, and also the proportionate ratio of 4 colors shows that each of 4 SM-FP donor plasmids recombined at similar efficiencies.

FIG. 5a) Schematics of plasmids and alleles subject to PCR analysis at denoted sites. Primers used are listed in Table 1. FIG. 5b) PCR screening analysis reveals that rtTA-V10-AU1 cassette is correctly integrated downstream of CAG-promoter in cells that are resistant to puromycin treatment FIG. 5c) Western blot analysis of the cell line from FIG. 4c showing the expression of rtTA-V10-AU1 and also EGFP upon doxycycline induction, and also illustrating that puromycin-resistant cells were expressing puromycin from Rosa26 locus, not from any other non-specific integrants.

FIG. 6a) At 2 days post-EP, cells start expressing TagBFP2. Scale bars: 50 µm; Insets: 10 µm. FIG. 6b) Gliogenesis and radial glia 2 weeks post-EP. Arrow indicates rare green-and-blue double positive cells at the VZ. Scale bars: 100 µm; Inset: 20 µm. FIG. 6c) High-magnification confocal image of a pair of TagBFP2+ satellite glia, which are negative for tdTomato and EGFP. Scale bars: 10 µm.

FIG. 7a) Brighter EGPF-Hras$^{G12V}$ cells after pBase-mediated integration express phosphorylated Rb1. Scale bars: 200 µm. FIG. 7b) Related to FIG. 1C and FIG. 7C; Scale bars: 1 mm. FIG. 7c) Zoom-in images of regions 1 and 2 from FIG. 7b) show phosphorylated-Rb1 expression correlates largely with blue only cells. Scale bars: 50 µm.

FIG. 8a) Two weeks post-EP shows clear lineage divergence between EGFP+ cells that underwent Cre-mediated excision of tdTomato cassette and HrasG12V+ cells with successful dRMCE. Scale bars: 100 µm. FIG. 8b) As low as 10 ng/µl recombinase-expression vector in EP mixture can catalyze dRMCE in vivo. Scale bars: 100 µm.

FIG. 9a) Lineage tracing of EP-ed cells in the VZ/SVZ with hyPBase-integrated EGFP reporter plus various donor vectors and recombinases do not show any hyperplasia by 2 weeks post-EP. Scale bars: 1001 µm FIG. 9b) Donor vector with inverted loxP orientation fails to express Hras$^{G12V}$ and does not produce hyperplasia. Scale bars: 100 µm. Sequences in the figure—top sequence loxP: ATAACTTCGTATAGCATACATTATACGAAGTTAT (SEQ ID NO: 19); bottom sequence loxP: ATAACTTCGTATAATGTATGCTATACGAAGTTAT (SEQ ID NO: 20).

FIG. 10a) At 3 months post-EP, cells expressing multi-miR-E tied to TagBFP2 reporter are predominantly Pdgfra+ OPCs. Scale bars: 100 µm. FIG. 10b) Olfactory bulb neurons stably expressing TagBFP2-multi-miR-E at 6 months post-EP shows no sign of aberrant transformation. Scale bar: 200 µm FIG. 10c) Multi-miR-E knockdown efficiency by mRNA quantification. Biological replicates were used. FIGS. 10d-10e) Episomal Cas9-mediated multiplex mutation of Nfl, Trp53, and Pten yield transformation of piggyBac-transposed EGFP+ cells into Olig2+ tumors localized near white matter tracts.

FIG. 11a) In vitro assessment of transgene expression after dRMCE in heterozygous mTmG mNSCs shows the coexpression of nuclear EGFP with Pdgfra, V5 (Trp53R270H), and P53. Note the presence of contaminating mG cells with membrane EGFP and no tdTomato or transgene expression. Scale bars: 50 µm. FIG. 11b) Confirmation of Trp53 co-expression with nuclear EGFP (H3f3a). Scale bars: 50 µm. FIG. 11c) Combined expression of MADR G34R/Pdgfra/Trp53 and a plasmid inducing CRISPR/Cas9-targeting of Atrx does not accelerate tumor formation. FIG. 11d) Atrx is expressed in the majority of EGFP+ cells in K27M tumors. A small subset of EGFP+ cells (yellow arrows) has lost Atrx antigenicity. FIG. 11e) G34R cells at 100 days post-EP express Atrx. FIG. 11f) CRISPR/Cas9 targeting leads to highly efficient loss of Atrx in EPed cells. FIG. 11g) Cortically-infiltrating G34R tumor at 120 days post-EP. Note the high Olig2 expression dorsally in tumor which is attenuated ventrally in the EGFP+ hyperplasia (yellow arrow). FIG. 11h) K27M tumor at 120 days post-EP is predominantly sub-cortical. i) A Cas9-mediated glioma derived from mutation of Nfl and Trp53 exhibits H3K27Me hypermethylation. FIG. 11i-1 shows staining pattern disparity at tumor margin. FIG. 11j) A monoclonal antibody demonstrates that expression of H3f3a transgene is consistent throughout Rosa26H3f3a-K27M/Pdgfra/Trp53 tumor. *-channel pseudocolored green from Cy5 wavelength for increased contrast.

FIG. 13a) Two weeks post-EP shows clear lineage divergence between EGFP+ cells that underwent Cre-mediated excision of tdTomato cassette and HrasG12V+ cells with successful MADR. Scale bars: 100 µm. FIG. 13b) As low as 10 ng/µl recombinase-expression vector in EP mixture can catalyze MADR in vivo. Scale bars: 100 µm. FIG. 13c) Brighter EGPF-HrasG12V cells after pBase-mediated integration express phosphorylated Rb1. Scale bars: 200 µm.

FIG. 14a) Schematic of donor plasmid for MADR of multiple recurrent pediatric glioma driver mutations. FIG. 14b) Representative tumor formation in heterozygous mTmG 100 days post-EP. Nuclear EGFP+ Rosa26H3f3a-K27M/Pdgfra/Trp53 cells form a large striatal tumor. Inset B-1 shows a lack of significant cortical infiltration. FIG. 14c) A littermate Rosa26H3f3aG34R/Pdgfra/Trp53 exhibits a glial hyperplasia in the striatum and a small mass of EGFP+ cells in the ventral forbrain medial to the piriform cortex. FIG. 14d) Rosa26H3f3aG34R/Pdgfra/Trp53 EGFP+ tumor cells are hypomethylated at H3K27. FIG. 14e) EGFP+ tumor cells exhibit variable H3f3a serine 31 phosphorylation at tumor margin versus the core. FIG. 14f-14g) Zoom-in images of regions FIG. 14e show that EGFP+ nuclear phosphorylated-serine 31 expression is higher in the tumor margin and attenuated in the core despite the increase in overall cell density in the core.

FIG. 15a) Plasmid for MADR of a TagBFP2-V5 reporter protein and SpCas9. FIG. 15b) tdTomato-/EGFP- glioma cells purified from tumor exhibit InDels in Nfl and Trp53. Sequences in the figure: Nfl1 Exon 42 AACTCCCTCGATGTGGCGGCT-CATCTGCCC (SEQ ID NO:15); AACTCCCTCGAATGTGGCGGCTCATCTGCCC (SEQ ID NO:16); Trp53 Exon 2 TCTCCTGGCTCAGAGG-GAGCTCGAGGCTG (SEQ ID NO:17); TCTCnnnnnnnA-GAGGGAGCTCGAGGCTG (SEQ ID NO 18). FIG. 15c) MADR insertion of TagBFP2-V5 reporter and Cas9 with co-EPed PCR-derived sgRNAs yields high grade glioma observable through genetic labeling of 3 recombinant lineages. FIG. 15d) Glioma cells are largely Olig2+ with small pockets of heterogeneity (white arrow). FIG. 15e) High magnification Olig2 and tdTomato image focusing on the region denoted by the white arrow in FIG. 15d. FIG. 15f) CD44 and tdTomato immunostaining in a roughly adjacent section and region from FIG. 15e demonstrating positivity for the CD44 mesenchymal tumor marker. FIG. 15g) Pdgfrb immunostaining of brain demonstrates that most pericytes are non-tumor derived (i.e. tdTomato+; $E_1$). FIG. $15G_2$) Clusters of tdTomato- pericytes can be observed in discrete regions. FIG. $15G_{3-5}$) Single z plane from G2 and subsequent enlargement thereof demonstrates the lack of colocalization of tdTomato and Pdgfrb (arrowhead). FIG. 15h) Des (aka Desmin) immunostaining of brain pericytes. $H_1$) Clusters of Des+ pericytes which do not colocalize with tdTomato. FIG. $15H_2$) Single z plane from projection seen in FIG. $15F_1$. *-channel pseudocolored green from Cy5 wavelength for increased contrast FIG. 16a) V5+ tumor-derived cell populations can be found juxtaposed to the Tdtomato+ vasculature in focal regions of the tumor. FIG. 16b) Pecam immunostaining of MADR brain with large glioma. FIG. $16c$-$16d_2$) Rare tdTomato-/Pecam1+ figures can be observed but do not link up to vasculature. FIG. 16e) Overexposure of red signal in panel from FIG. $16F_2$ similarly demonstrates a lack of colocalization between tdTomato and Des. FIG. 16f) Des signal in most regions of tumor exhibits a perivascular pattern and co-localizes with tdTomato even when not clearly associated with vessels (white arrows). *-channel pseudocolored green from Cy5 wavelength for increased contrast

DESCRIPTION OF THE INVENTION

Figure 1:
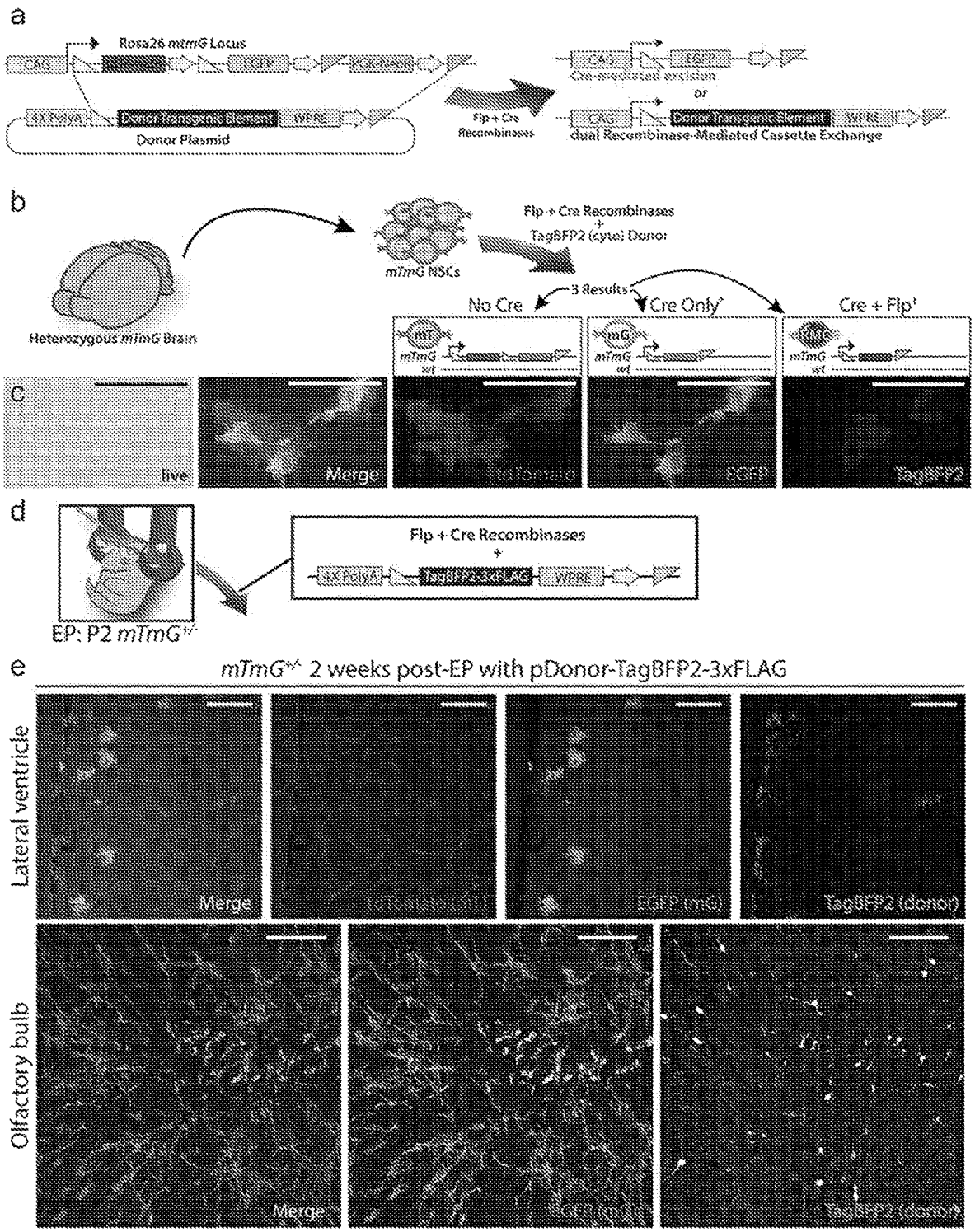
Figure 1:
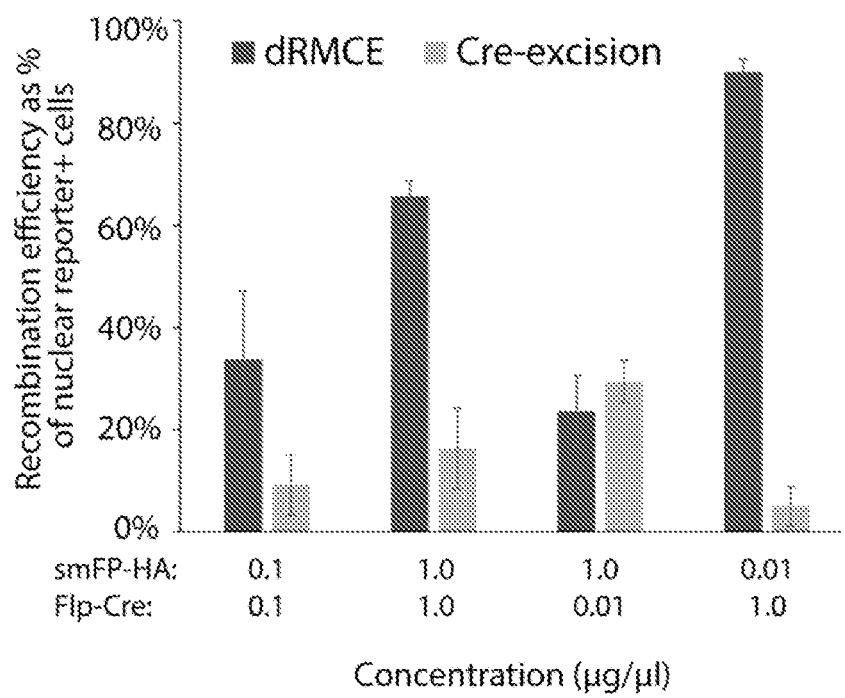

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., Revised, J. Wiley & Sons (New York, N.Y. 2006); and Sambrook and Russel, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

With the unbiased identification of nearly 300 recurrent, putative cancer driver mutations, many of which are GOF oncogenes, it is imperative to create a tractable in vivo platform that can model these cancer drivers. For loss-of-function (LOF) mutations in tumor suppressors, large-scale knockout (KO) mice consortia now offer immediate access to relevant GEMMs, but modeling a tumor with multiple KOs will require many floxed alleles that can recombine independently, complicating the results. In light of this, CRISPR/Cas9-based studies have now demonstrated the ability to induce multiple KOs in vivo in mice. For GOF mutations, however, it remains a daunting prospect to compile an exhaustive catalogue of necessary GEMMs.

Focusing on the CNV, positional variability, and insertional mutagenesis problems of non-GEMM models, we sought a method that can ensure uniform gene dosage among transfected cells and thus looked to dRMCE (also discussed herein as mosaic analysis by dual recombinase-mediated cassette exchange (MADR)), which has been explored as an efficient knock-in method. Conventionally, this method necessitates antibiotic clonal selection and Southern probing of positive integrants, typically mouse embryonic stem cells (mESCs). With appropriate safeguards, we demonstrate that successful dRMCE can be catalyzed in situ in somatic cells, using an off-the-shelf reporter mouse Rosa26mTmG (mTmG) with definitive genetic labeling of recombined cells (FIG. 1a). Moreover, we demonstrate the utility of this system in generating mosaics with a mix of GOF and LOF mutations, including patient-specific cancer driver mutations. As a non-GEMM method for tumor modeling, this procedure can serve as a superior, fast pipeline for preclinical drug discovery in a patient-specific manner.

Figure 2:
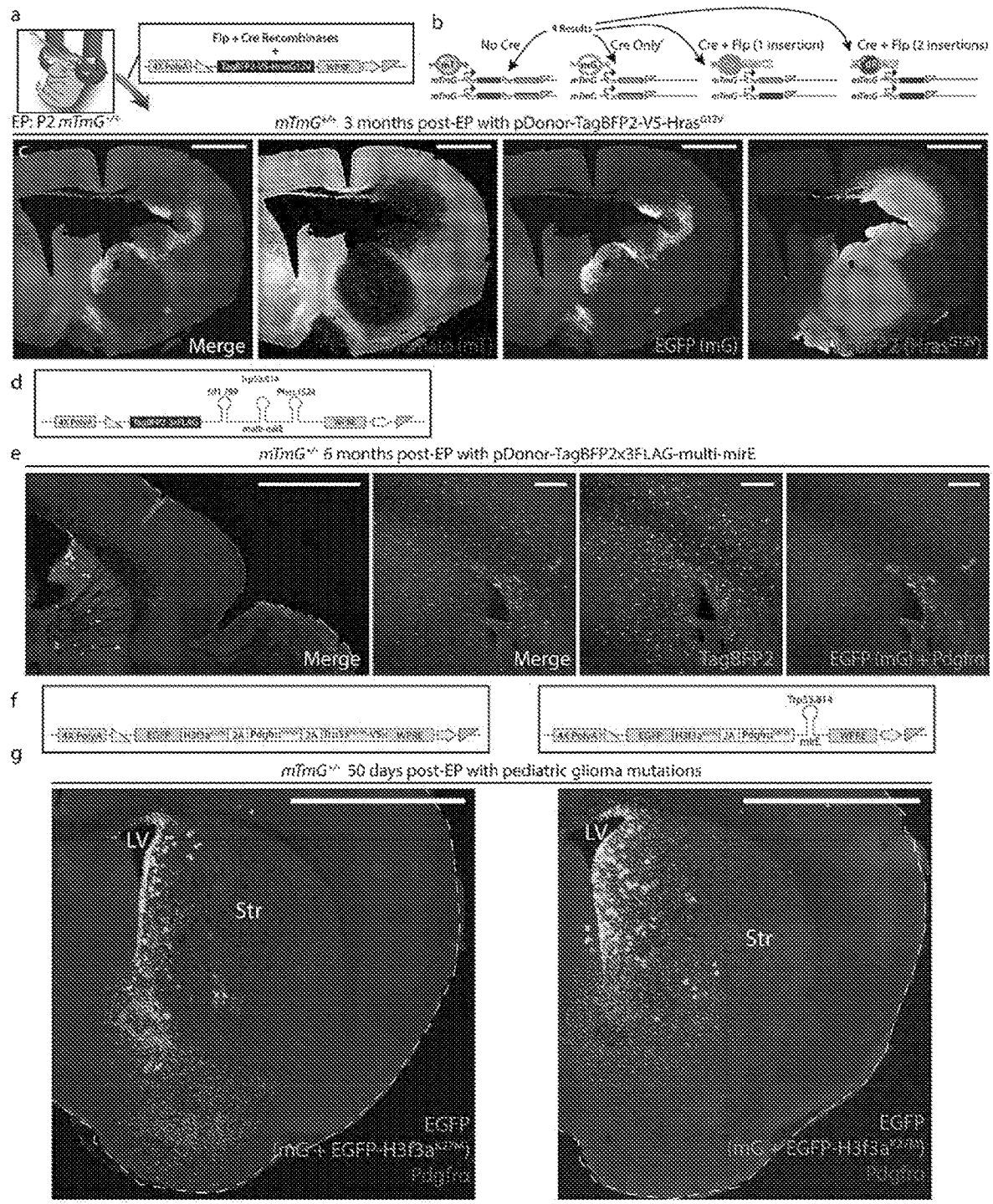
FIGS. 2A-2J show that rapid generation of somatic mosaics using in vivo dRMCE can be used for autochthonous tumor modeling in accordance with various embodiments of the present invention.
Figure 2:
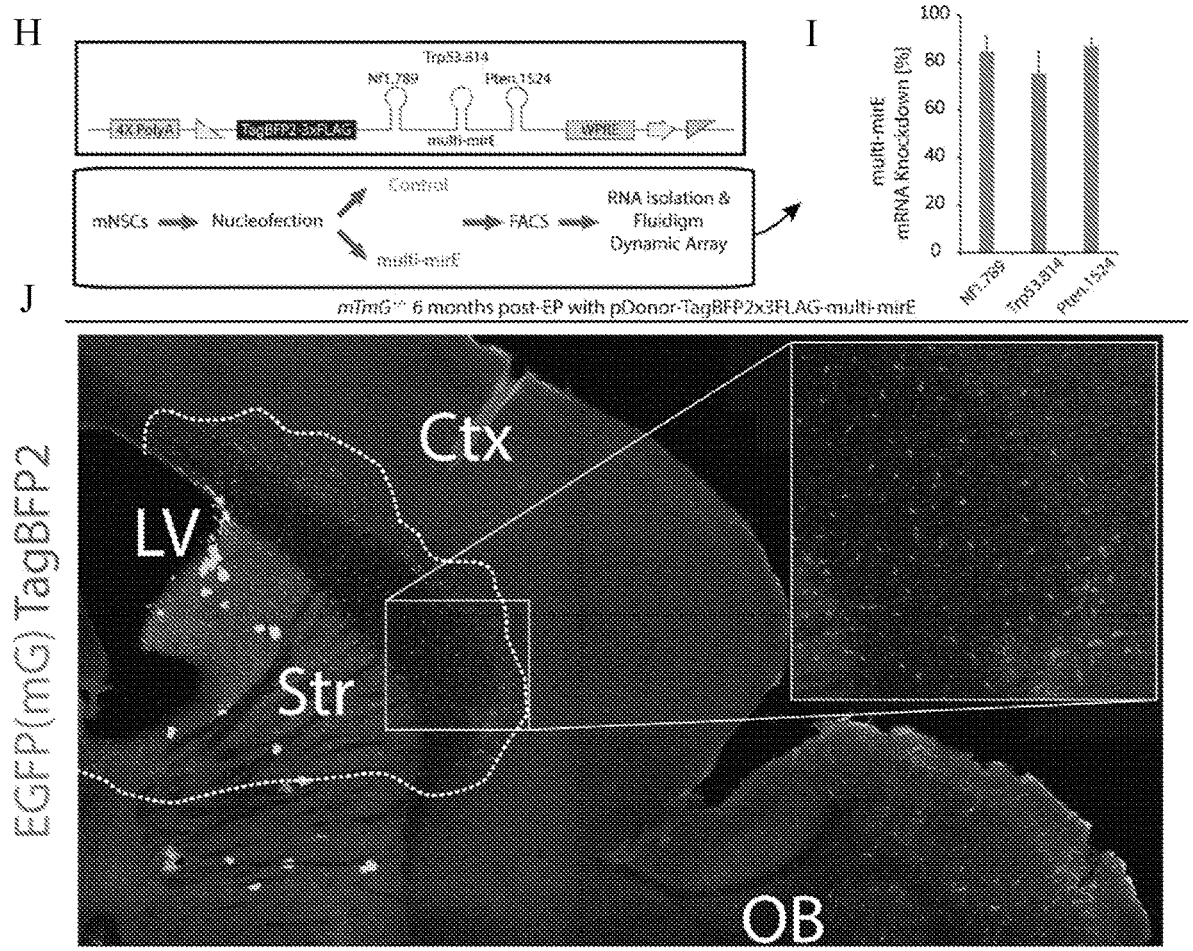
Figure 3:
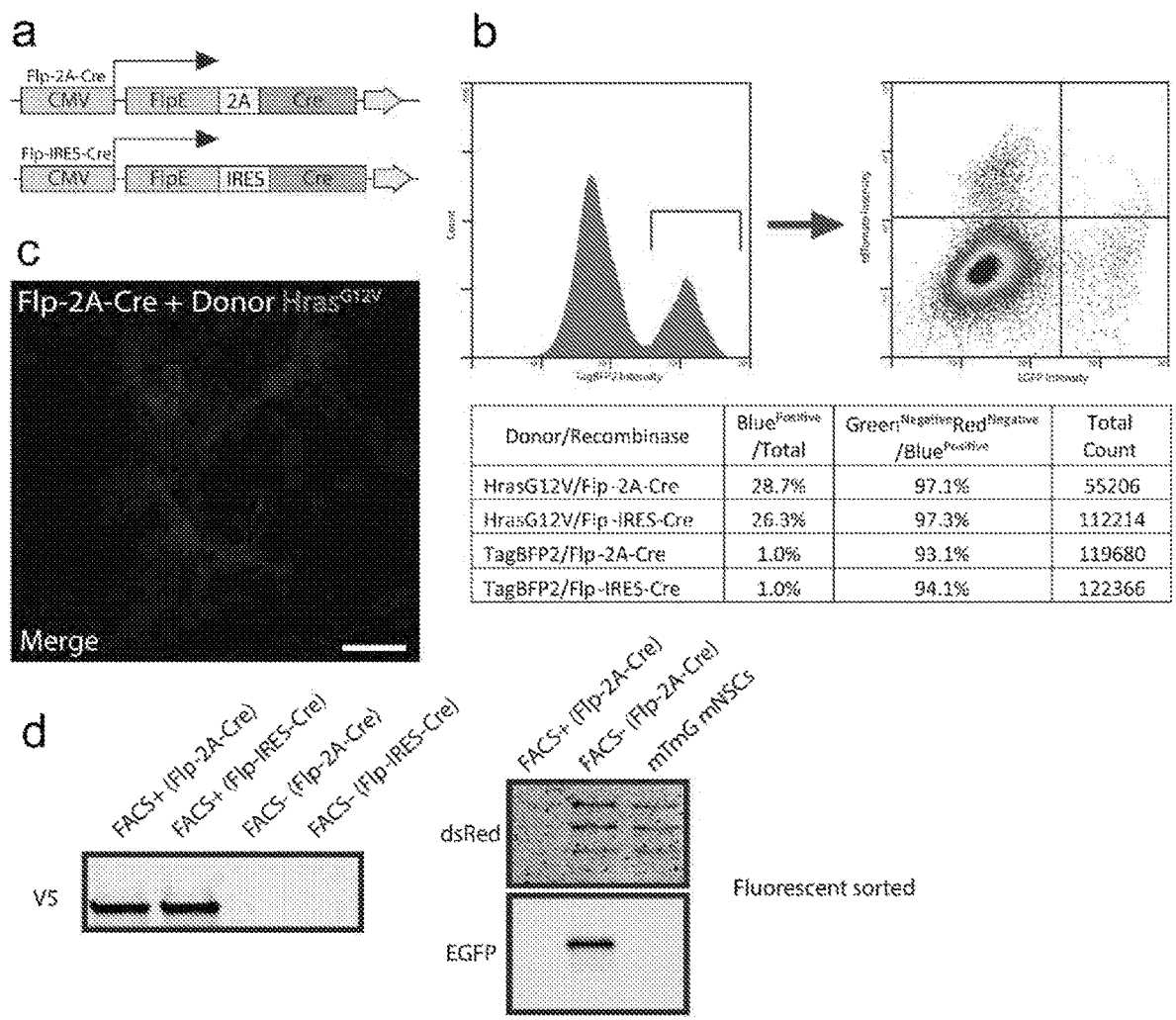
FIGS. 3A-3D depict measurement of dRMCE efficiency in heterozygous mTmG mNSCs by FACS analysis, and confirmation of correct protein translation at non-clonal population level in accordance with various embodiments of the present invention.

Rosa26mTmG is a widely used reporter line that constitutively expresses membrane tdTomato and switches to EGFP expression upon Cre-mediated excision of tdTomato cassette. In order to accommodate dRMCE in mTmG, we utilized the unused blue fluorescence channel and created a promoter-less donor plasmid encoding TagBFP2, as well as TagBFP2-tagged HrasG12V, flanked by loxP and FRT sites (FIG. 1d and FIG. 2a). Both mTmG and TagBFP2 plasmid contain minimal 34-bp FRT, which is refractory to Flp-mediated integration. Briefly, the open reading frame (ORF) is preceded by PGK polyadenylation signal (pA) and trimerized SV40 pA that will preempt spurious transcription from unintegrated episomes and randomly integrated whole-plasmids, which is known to occur with electrochemical transfections. The ORF is followed by woodchuck hepatitis virus post-transcriptional regulatory element (WPRE), which increases transgene expression and a rabbit beta-globin pA, which efficiently terminates transcription (FIG. 1a). We generated heterozygous Rosa26WT/mTmG mice (mTmGHet) and subsequently established a mouse neural stem cell line (mNSC) that carries a single mTmG allele. dRMCE with TagBFP2 donor plasmid and Flp-Cre expression vector gave rise to three possible results, with cells remaining tdTomato+ or turning green or blue (FIG. 1b,c and FIG. 3a). One week after nucleofection with either TagBFP2 or HrasG12V plasmids, FACS analysis indicated the rapid proliferation of HrasG12V cells and also approximate efficiency of dRMCE in mNSCs at around 1% (FIG. 3b). On average, 5% of cells positive for blue fluorescence retained either green or red fluorescence, which can be explained by the relatively slow degradation kinetics of membrane tdTomato (FIG. 3b,c). After another week of culturing sorted cells, we performed western blot and confirmed the absence of residual EGFP or tdTomato expression and also correct HrasG12V expression, indicating that the recombined Rosa26 locus generates the correct polypeptide even at the aggregate, nonclonal population level (FIG. 3d).

Figure 4:
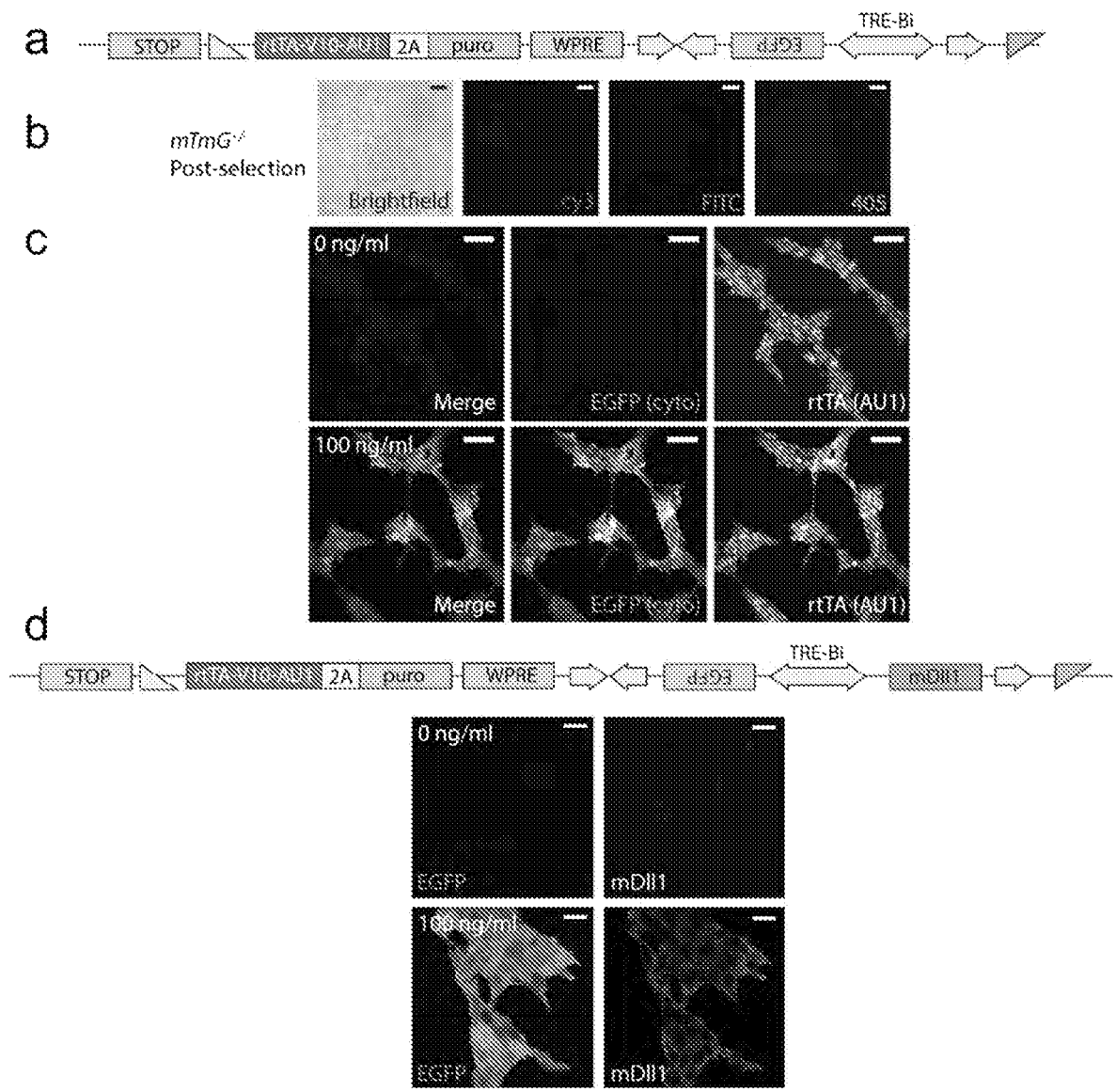
FIG. 4A-4G depict dRMCE-compatible inducible donor construct that can be used to interrogate overexpression and GOF mutations of genes in accordance with various embodiments of the present invention.
Figure 4:
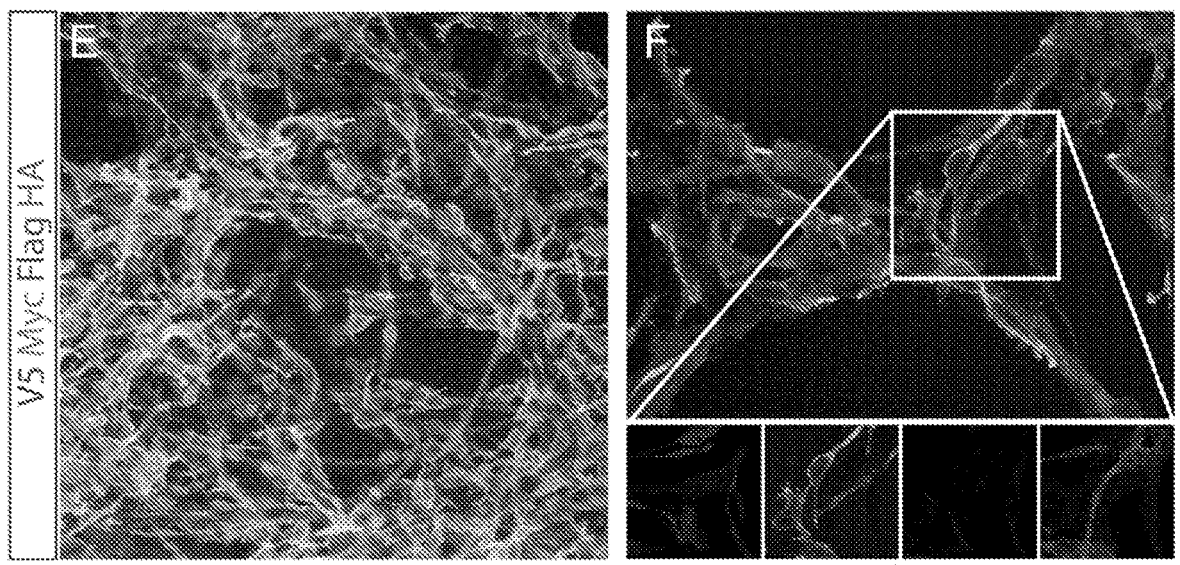
Figure 4:
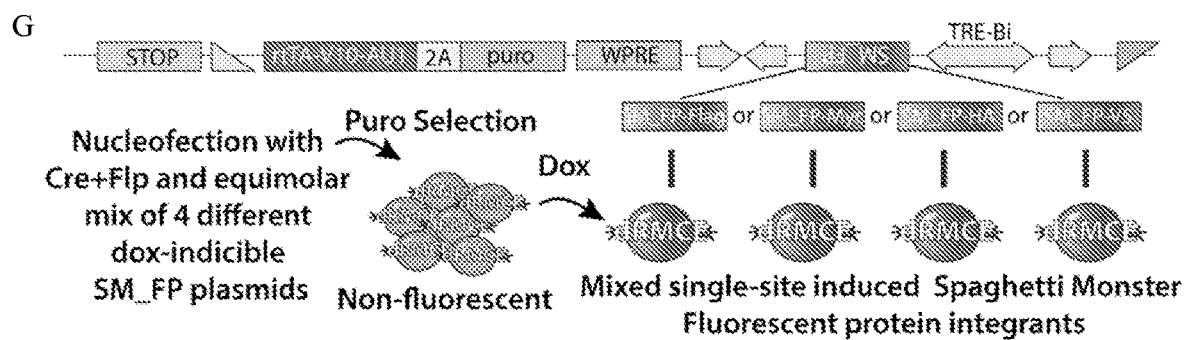
Figure 5:
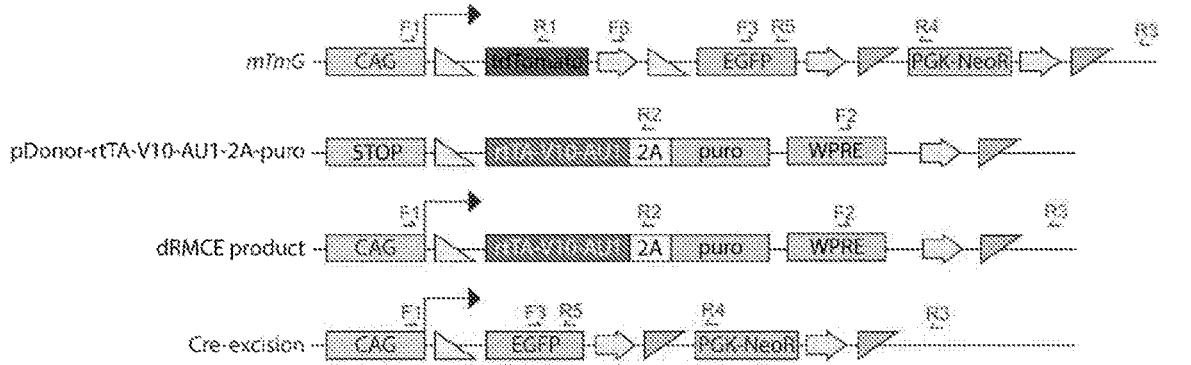
FIGS. 5A-5C depict PCR screening and western blot analysis confirming dRMCE-mediated excision of tdTomato cassette and integration of donor cassette at Rosa26mTmG locus in accordance with various embodiments of the present invention.
Figure 5:
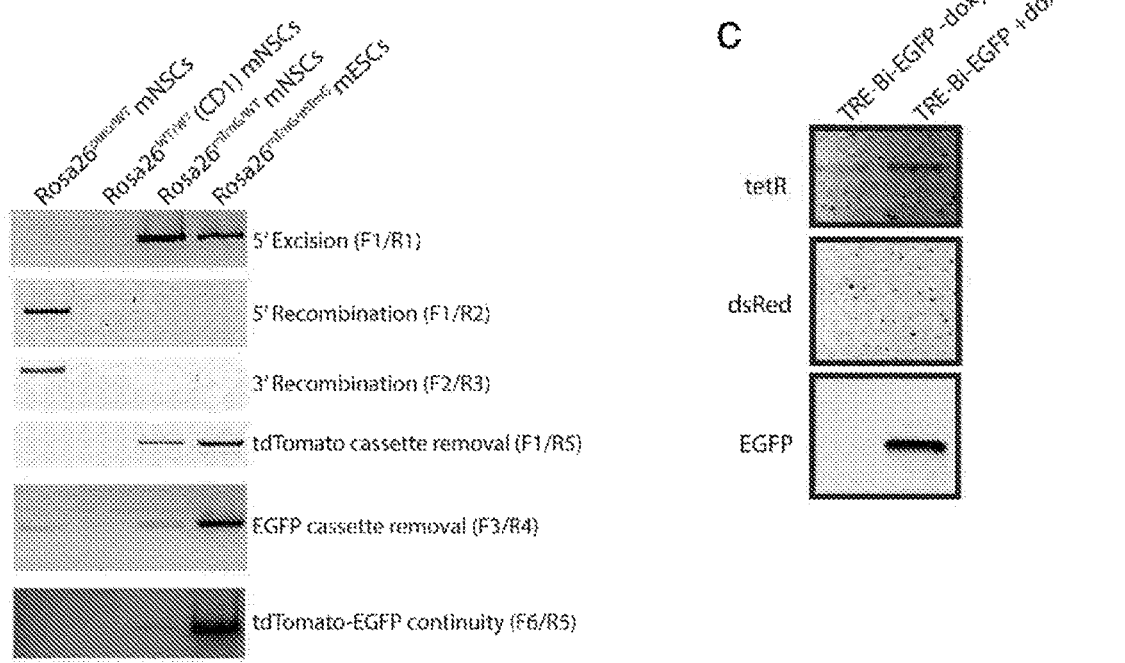
Figure 5:
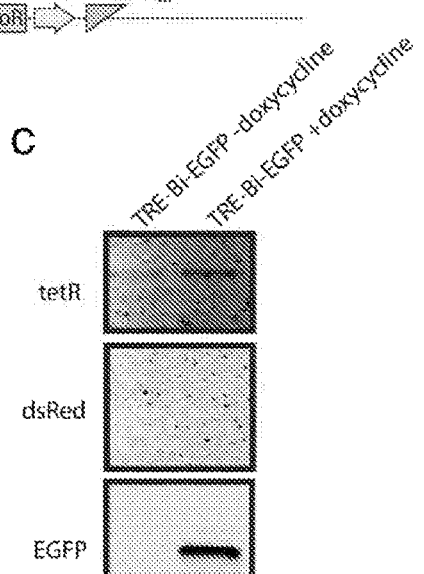

Evaluating GOF proteins are often accomplished in vitro but constitutive transgene expression can be detrimental to stable cell line generation. To obviate this issue, inducible genetic systems, such as TRE, are sometimes employed. To expand the utility of single-allele mTmGHet mNSCs, we aimed to create a pipeline for inducible cell line production by creating a single dRMCE-compatible plasmid containing rtTA-V10 and TRE-Bi element (FIG. 4a). Subsequently, we generated a colorless TRE-Bi-EGFP cell line with puromycin selection and confirmed the fidelity of TRE with the standard in vitro dox treatment (FIG. 4b,c). We also generated a cell line that expresses uniform levels of the Notch ligand Dll1 expression with a bicistronic TRE-Bi-Dll1/EGFP donor vector because we have noted changes in the subcellular distribution with CNV (data not shown; FIG. 4d). Using a cloning intermediate plasmid that expresses only puromycin, we also checked for the correct recombination at Rosa26 locus by PCR screening (FIG. 5a,b and Table 1). After dRMCE, the tdTomato cassette no longer resides downstream of the CAG-promoter upon dRMCE. However, PCR screening revealed the perdurance of the EGFP cistron in some cells, but the expression of EGFP is mitigated by the upstream polyA elements and the distance from the CAG-promoter (FIG. 5b). Supporting this, we did not observe EGFP autofluorescence, and western blot of these cells showed EGFP expression only with doxycycline treatment (FIG. 4b and FIG. 5c).

Given the lack of EGFP expression after puro selection in the TRE-Bi-EGFP cell line, we reasoned that we could use similar Dox-inducible plasmids to express four different "spaghetti monster" fluorescent proteins (SM_FPs), which allow for orthogonal detection through their different epitope tags. We used MADR with multiply-antigenic XFPs (MADR MAX) to empirically assess whether more than one copy of each plasmid could be expressed per cell (FIG. 2g). Specifically, expression of more than of these high signal-to-noise SM_FP probes per cell would be easily detectable by immunofluorescence. Examining hundreds of cells displayed the presence of the SM_FPs in virtually all cells after puro selection and Dox addition (FIG. 4e). However, at high magnification, we did not observe any cells expressing more than one SM_FP by immunofluorescence (FIG. 4f), indicating that the dRMCE methodology mediates single copy insertion of transgenic elements.

This in vitro system will be beneficial to interrogating GOF protein functions in various primary cell lines derived from any animal carrying loxP and Frt by providing more homogeneous, inducible stable cell lines. As proof-of-principle for this, and to empirically test the utility of the potential leakiness of the 3' cistron of the TRE-Bi element—which could potentially be activated by upstream promoters or enhancers-we also generated a cell line that inducibly expresses the Notch signaling ligand, Dll1, with a bicistronic TRE-Bi-Dll1/EGFP donor vector (FIG. 4d). Notably, there was no readily detectable reporter and minute levels ligand present without Dox but when added, both EGFP and Dll1 were expressed at virtually similar levels by all cells (FIG. 4d). (The minute amount of ligand expression in the absence of Dox was comparable to the endogenous expression of mNSCs.) Notch signaling is one example of molecular pathways that gene-dosage sensitive, and our pipeline could be purposed for studying pathways such as this.

TABLE 1

Primers used for PCR screening

| | | | SEQ ID NO: |
|---|---|---|---|
| F1 | GCAACGTGCTGGTTATTGTGC | mtmg-cagF | 1 |
| F2 | CTCAATCCAGCGGACCTTCC | mtmg-wpreF | 2 |
| F3 | AGCAAAGACCCCAACGAGAAG | EGFP-F | 3 |
| F4 | TGTCTGGATCCCCATCAAGC | mtmg-sv40F | 4 |
| F5 | ATGCCCTGGCTCACAAATAC | rb glob pA F | 5 |
| F6 | ACACAGGCATAGAGTGTC | SV40pA-F | 6 |
| R1 | GATGACGGCCATGTTGTTGTCC | mtmg-tdtomatoR2 | 7 |
| R2 | TTTAACAGAGAGAAGTTCGTGGC | pTV-R | 8 |
| R3 | GGAGCGGGAGAAATGGATATG | Rosa26-wildtype-R | 9 |
| R4 | CGAAAGGCCCGGAGATGAGGAAG | PGKpromR | 10 |
| R5 | TGATCGCGCTTCTCGTTGGG | EGFP653CSseq | 11 |

Figure 6:
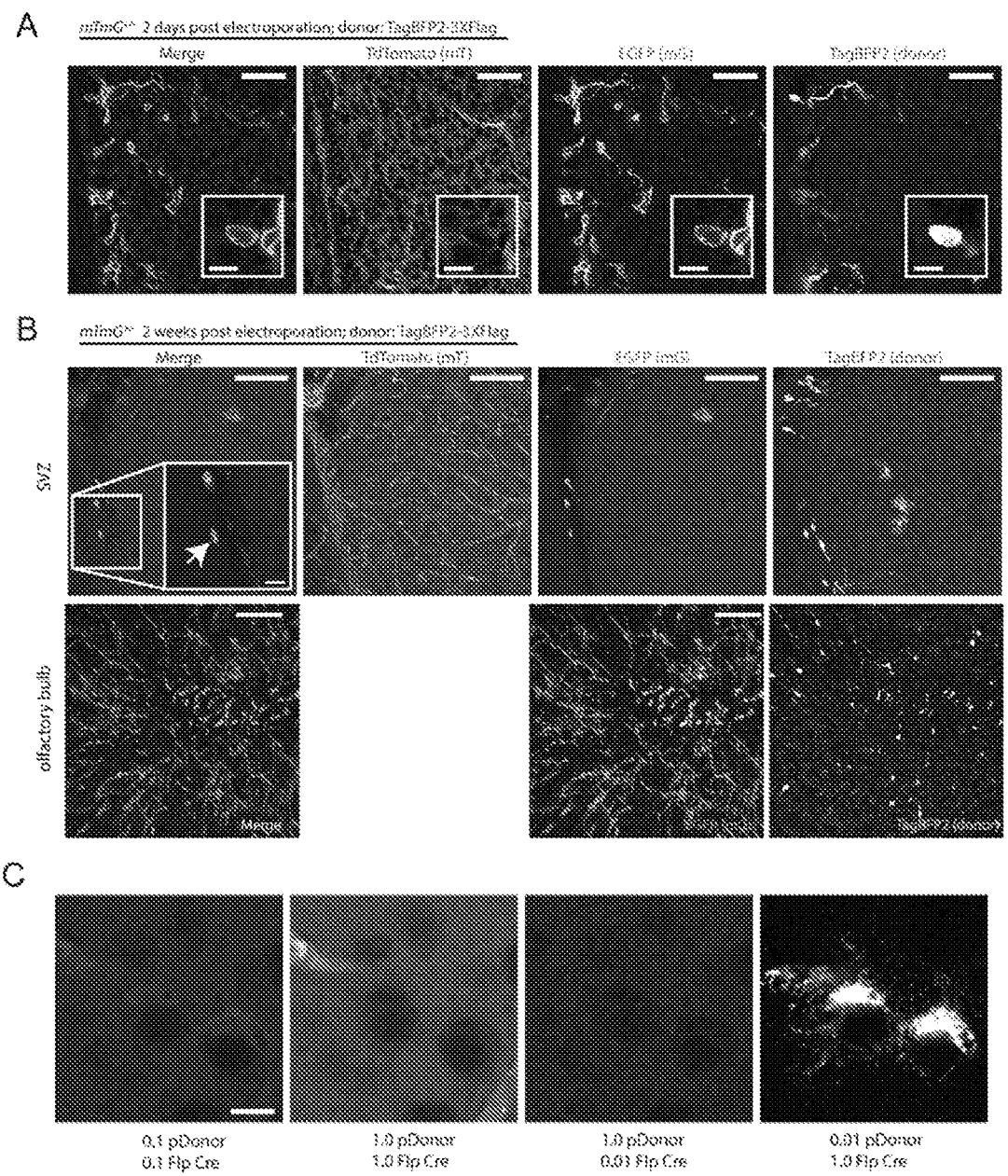
FIGS. 6A-6C show that in vivo dRMCE in VZ/SVZ is detectable at 2 days and stable at 2 weeks post-EP with subsequent removal of membrane-tdTomato expression in accordance with various embodiments of the present invention.
Figure 7:
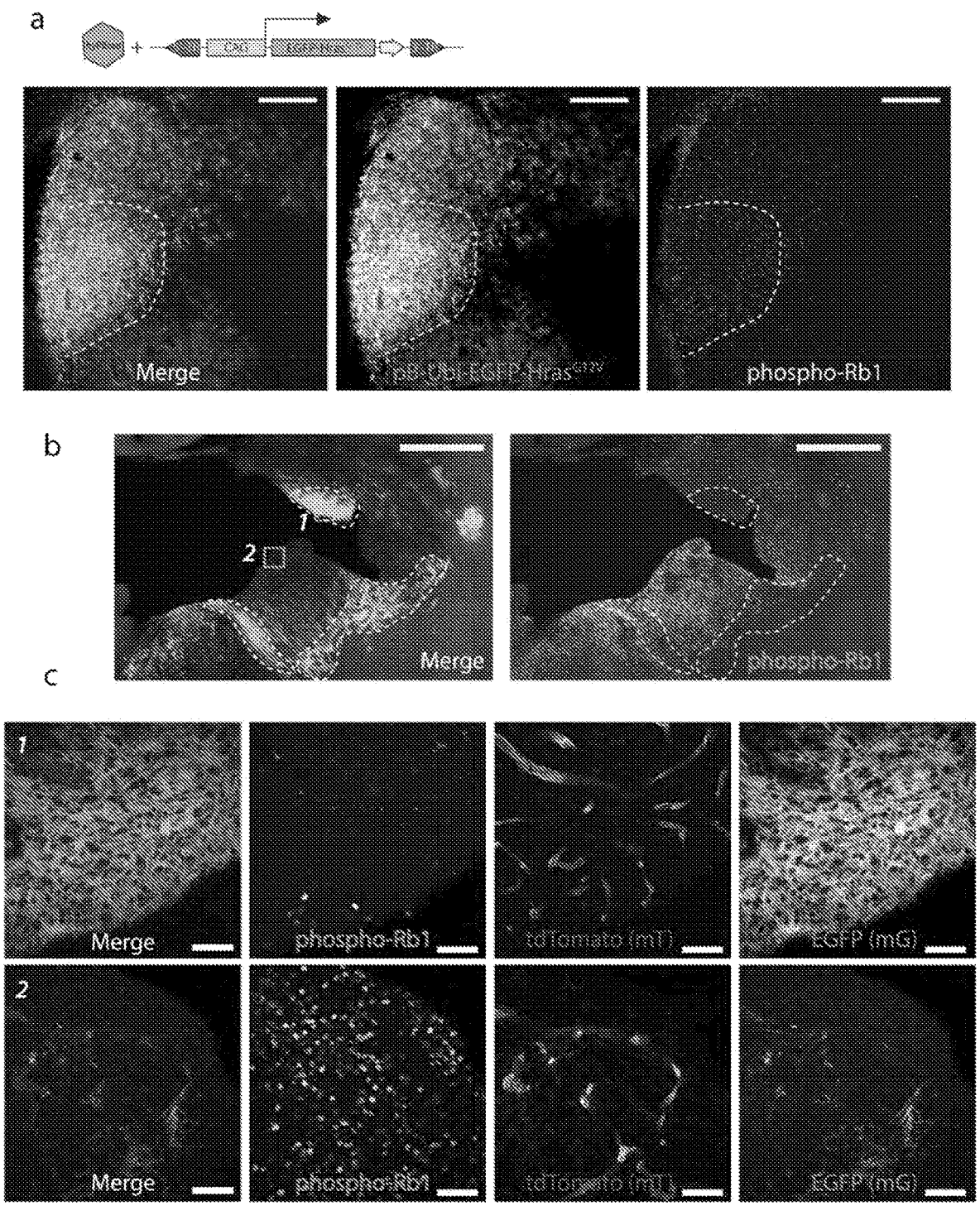
FIGS. 7A-7C show that Hras$^{G12V}$ confers gene-dosage-dependent differential phenotypes in accordance with various embodiments of the present invention.

To investigate the applicability of in vivo dRMCE, we EP-ed into the neural stem/progenitor cells lining the VZ/SVZ of postnatal mTmGHet pups with TagBFP2 donor vector with Flp-Cre expression vector (FIG. 1d). Accordingly, we noted the appearance of recombined cells along the VZ as early as 2 days after EP, and these cells gave rise to olfactory bulb neurons and glia by 2 weeks (FIG. 1e and FIG. 6a-c). Confocal analysis of TagBFP+ satellite glia shows the absence of tdTomato and EGFP expressions in these cells (FIG. 6c). We noticed some rare TagBFP2+ cells with persistent EGFP expression at the VZ, and these cells could be ependymal-lineage cells with slow protein processing kinetics (FIG. 6b). All four of the homozygous mTmG EP-ed with HrasG12V rapidly developed glioma and reached morbidity within 3-4 months (FIG. 2a-c). Using the same oncogene driven by the CAG-promoter, we have previously shown that PB-EP of HrasG12V results in 100% penetrant glioma. Interestingly, in our homozygous mTmG gliomas, blue-only cells (Rosa26HrasG12V×2) occupied a bigger patch of tumor cross-section than cells expressing both blue and green (Rosa26HrasG12V×1) (FIG. 2b,c). Previously, HrasG12V copy number has been shown to confer phenotypic differences, such as growth and apoptosis rates. Using PB-EP, we also observe that the brighter EGFP-tagged HrasG12V cells express phosphorylated Rb1 (pRb1) more than the dimmer EGFP+ cells (FIG. 7a). Similarly, most of the Rosa26HrasG12V×2 cells in mTmG EP-ed with HrasG12V seem to express pRb1, whereas Rosa26HrasG12V×1 do not (FIG. 7b,c). This data points to a possibility that the copy number of oncogenes can significantly alter the profile of resulting tumor populations, as previously observed using GEMMs.

However, most TagBFP2+ cells exhibited an absence of tdTomato and EGFP expressions by 2 weeks post-EP (FIG. 6C). To empirically test the effect of plasmid concentrations on the in vivo recombination efficiencies, we varied the concentrations of Flp-Cre recombinase-expression plasmid and MADR MAX reporter plasmid (i.e., expressing a spaghetti-monster reporter plasmid with ten HA-Tags) for high-sensitivity detection of recombined cells (FIG. 1f). Because the MADR (and, thus, MADR MAX) reaction is theoretically irreversible, we examined the brains 2-days post-EP. All DNA mixtures contained a non-MADR, constitutive nuclear TagBfp2 reporter. Surprisingly, we noted that lowering the donor plasmid concentration to 10 ng/µl approached nearly 100% MADR MAX efficiency and almost zero Cre-recombined cells with EGFP expression (FIG. 1f). One possible explanation is that increasing the concentration of donor plasmid, hence also of loxP and FRT recombination sites, competes for the recombinases. Alternately, an "overproduction inhibition" mechanism as is seen with transposases is another possibility. All subsequent electroporation mixtures contained 0.5-1 µg/µl of plasmids, in order to generate roughly equivalent numbers of EGFP cells and MADR or MADR MAX cells for side-by-side comparison.

Figure 8:
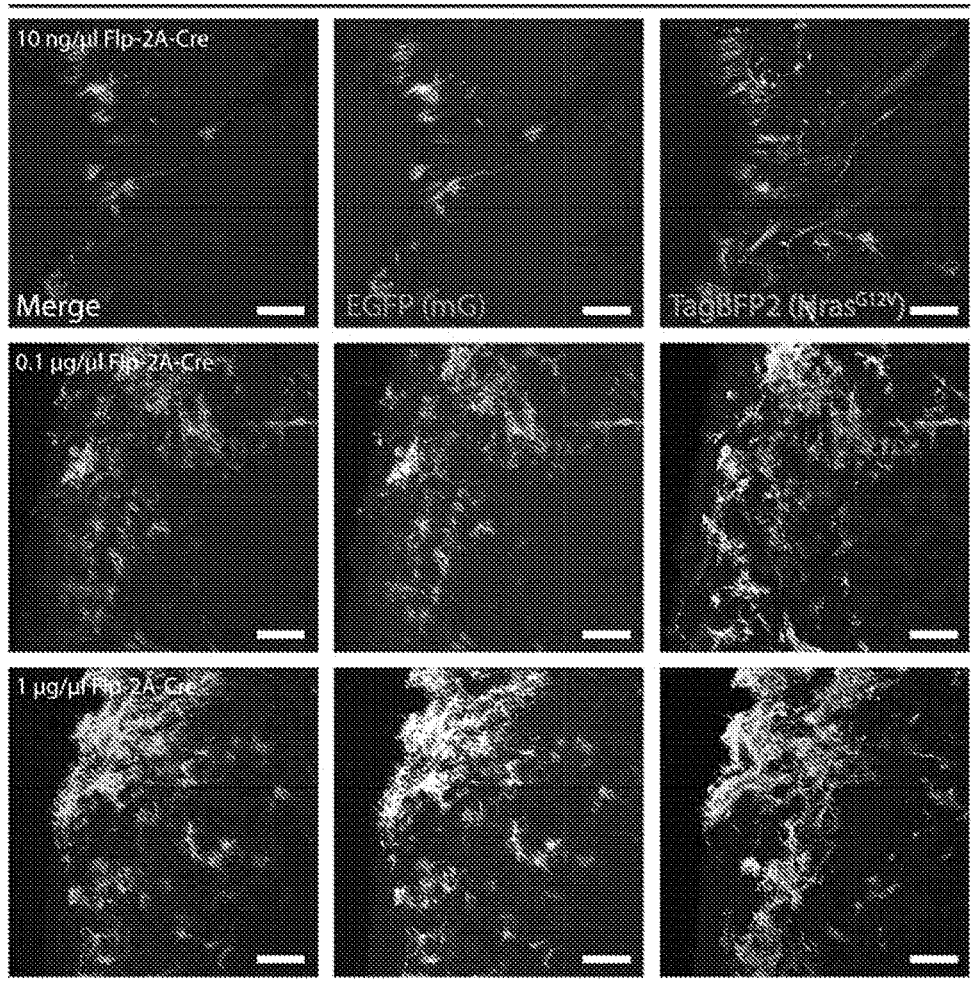
FIGS. 8A-8B depict examination of Hras$^{G12V}$-recombined mTmG cells in the striatum in accordance with various embodiments of the present invention.
Figure 9:
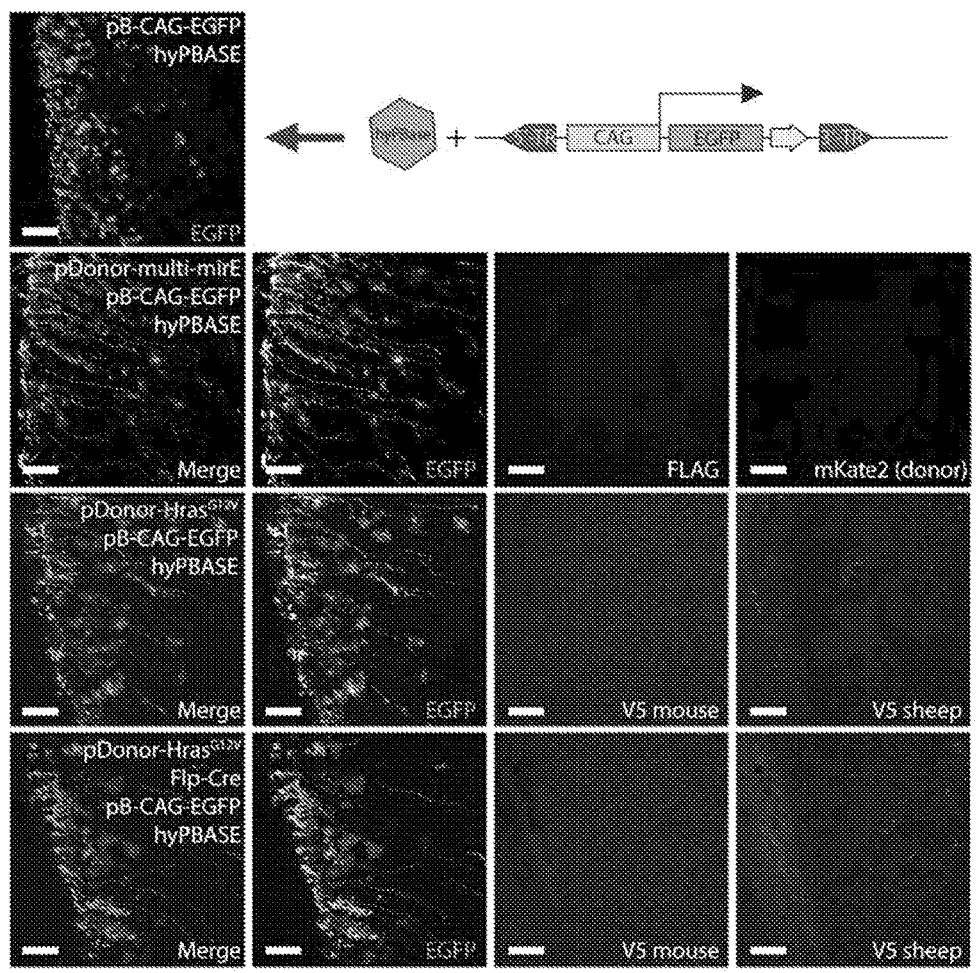
FIGS. 9A-9B depict control electroporation experiments for in vivo dRMCE in accordance with various embodiments of the present invention.
Figure 9:
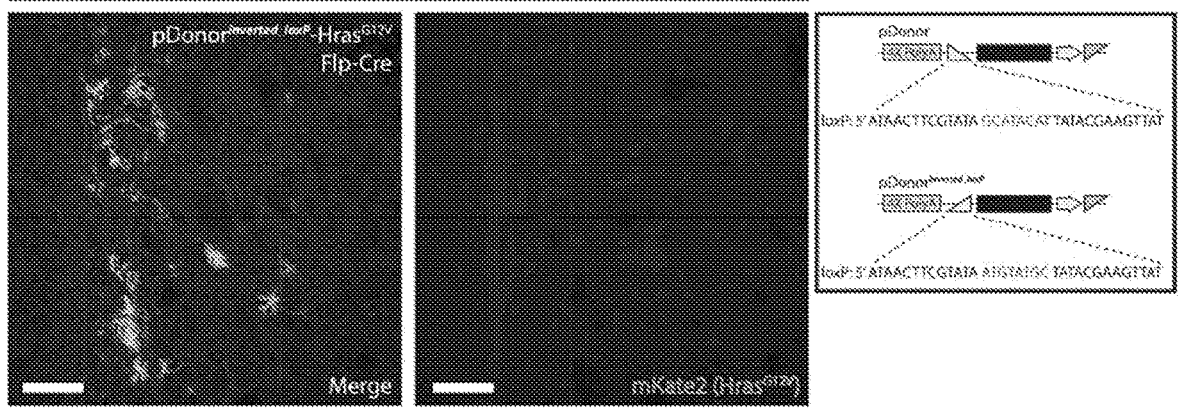

In mTmGHet with HrasG12V, we saw a tumorigenic growth of blue recombined cells (i.e., single-copy HrasG12V), but green sibling cells that underwent only Cre-recombination (i.e., without HrasG12V) did not display any abnormal growth (FIG. 8a). These green sibling cells could serve as useful control cell population in a manner akin to the wild-type cells in MADM22. MADM and MASTR allow rigorous, Drosophila-like deciphering of mutant cells but require de novo GEMM generation depending on the chromosomal location of GOIs. Because of its high proliferative capacity, HrasG12V mixed with as low as 10 ng/µl of recombinase expression vector still resulted in aggressive, early-onset tumorigenesis (FIG. 8b). In order to rule out tumor formation due to the expression from randomly integrated or non-recombined episomes, we performed a series of control electroporations (FIG. 9). First, EP of a concentrated mixture of donor HrasG12V (~5 µg/µl) into wild-type CD1 pups, combined with a PB-EGFP plasmid that marks the lineage of transduced cells, resulted in no abnormal growth, hyperplasia, or tumorigenesis regardless of the presence of Flp and Cre recombinases (FIG. 9a). In addition, we EP-ed mTmG pups with HrasG12V harboring an inverted loxP and failed to detect any blue recombined cells or hyperplasia by immunostaining, illustrating the specificity of dRMCE recombination reaction in vivo (FIG. 9b). Several independent EPs of the HrasG12V donor plasmid and Cre-recombinase alone failed to produce tumor formation when examined at 2 weeks post-EP, indicating that the Flp-excision is an extremely critical step for efficient in vivo dRMCE reaction and Cre is insufficient for sustained transgene integration by itself (Data not shown). Since Flp-excision is critical to the establishment of irreversible equilibrium, replacing FlpE with FlpO, to increase the efficiency of Flp-excision is another embodiment of the present invention.

Figure 10:
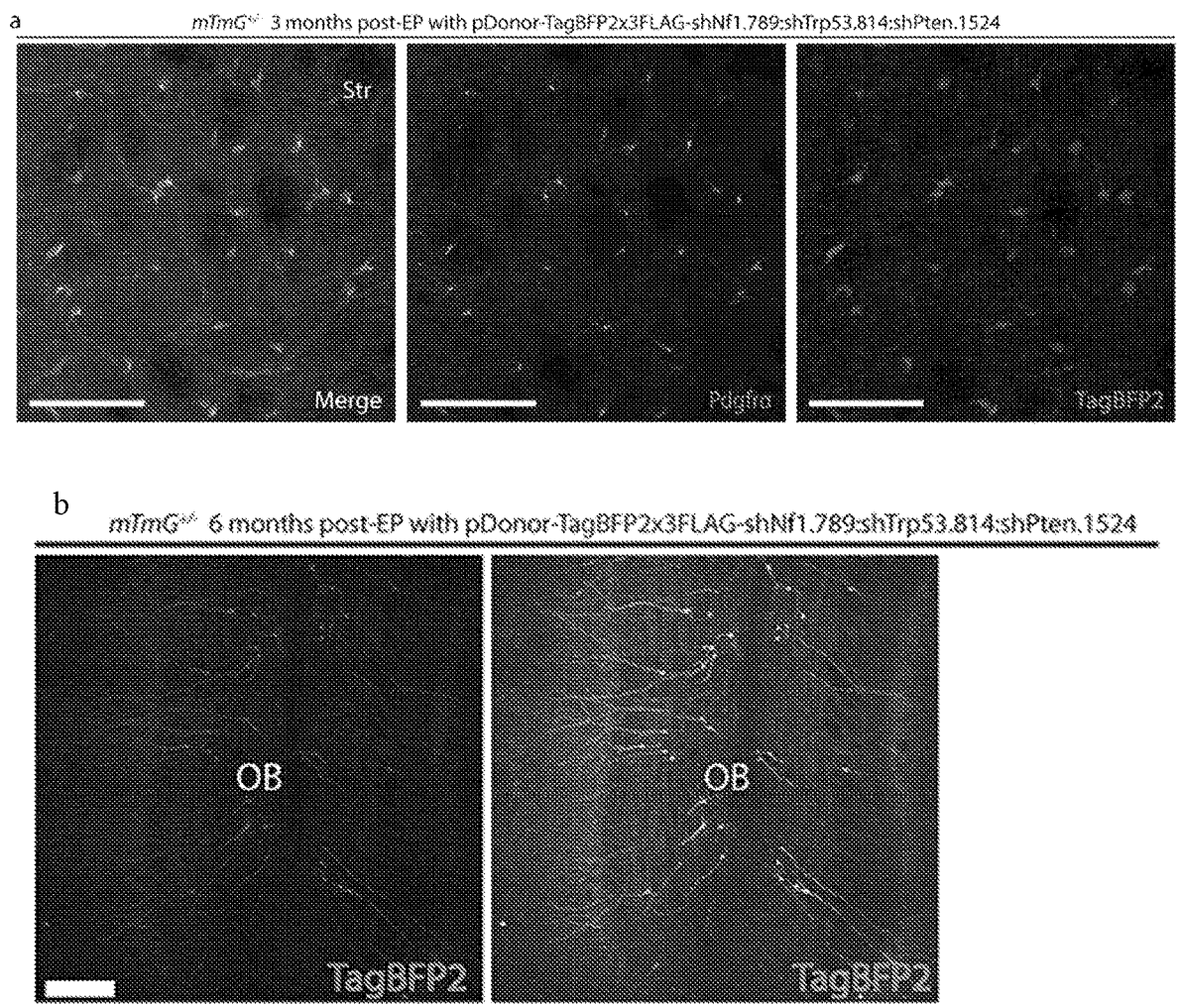
FIGS. 10A-10E depict knockdown of Nfl, Pten, and Trp53 mRNAs by qPCR, and the dormancy of these mutations in neuronal lineage in accordance with various embodiments of the present invention.
Figure 10:
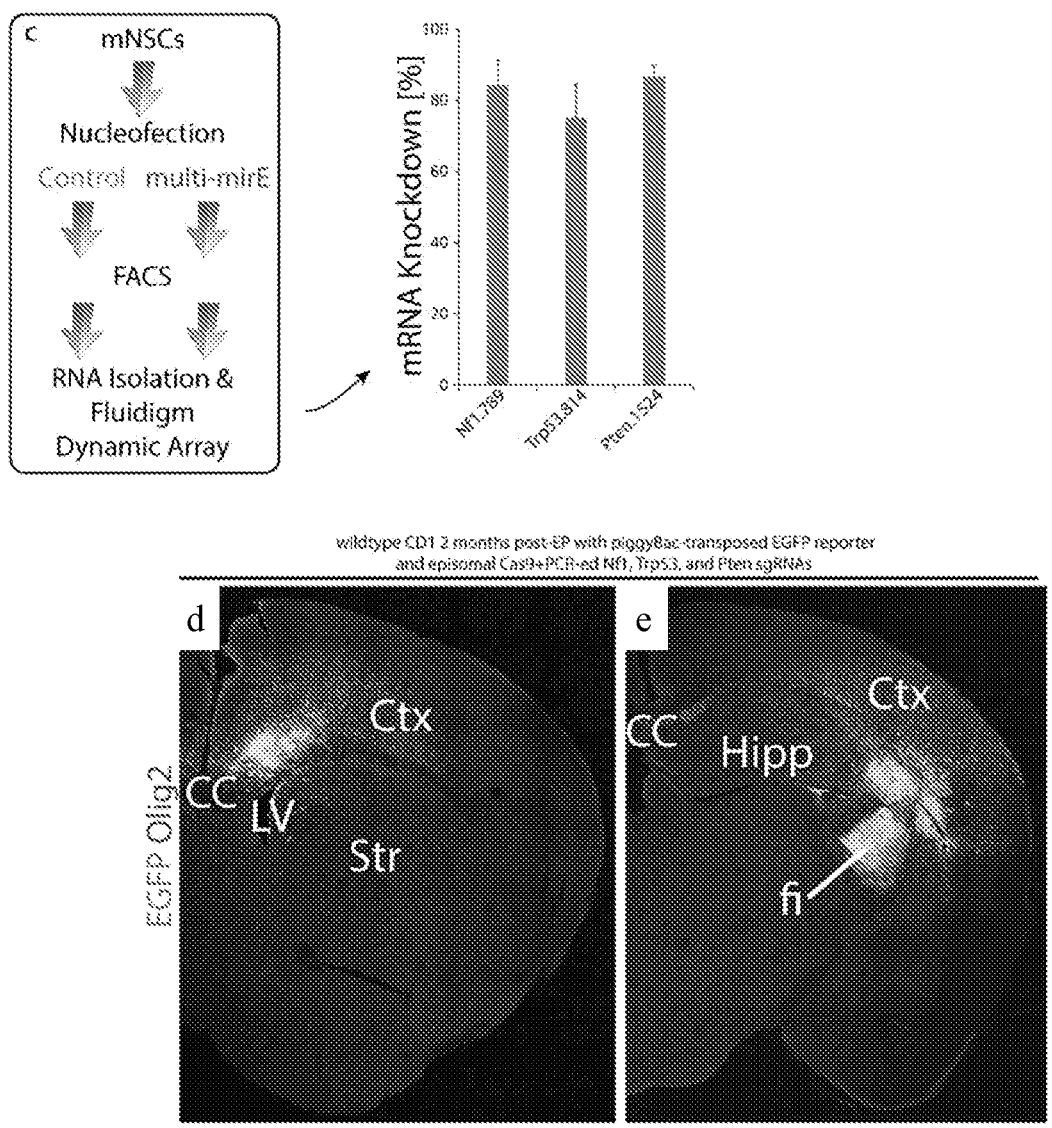

MADM has shown that the combined Trp53- and Nf1-LOF mutations promote the pre-malignancy hyperproliferation of oligodendrocyte progenitors (OPCs). We aimed to mimic a similar developmental phenomenon using our method. First, we created a donor construct harboring three contiguous validated miR-E-based shRNAs targeted at Nf1, Pten, and Trp53 tied to TagBFP2 expression (FIG. 2d). We tested this multi-miR-E construct and observed mRNA-level knockdown efficiency around 80%, comparable to the original report on miR-E (FIG. 10b,c). In agreement with the MADM findings, we observed the selective over-growth of TagBFP2+/Pdgfra+ OPCs, aligning with previous observations that LOF models based on Nf1 and Trp53 result in OPC-driven hyperplasia (FIG. 2e and FIG. 10a). We also observed that the expression of three miR-Es in OB neurons did not abrogate their morphologies or apparent cell types, also agreeing with the previous studies that the cell context is important for the transforming ability of these LOF mutations, whereby they become dormant in neuronal lineage cells (FIG. 10b). We did not detect any malignancy 200 days post-EP, indicating that the complete ablation of Trp53 is likely required for highly penetrant, early-onset tumorigenesis (FIG. 10c). As additional embodiments of the present invention, the system can be modified by creating a donor plasmid carrying spCas9 and delivering it with sgRNAs targeting tumor suppressors.

Given the ability of our MADR system to independently lineage trace multiple populations of GOF and LOF cells in vivo, we reasoned that it might be useful for studying glial development. It was elegantly demonstrated using MADM that the combined Trp53- and Nf1-LOF mutations promote the pre-malignancy hyperproliferation of oligodendrocyte progenitors (OPCs). We aimed to mimic a similar developmental phenomenon using our method. First, we created a donor construct harboring three contiguous validated miR-E-based shRNAs targeted at Nf1, Pten, and Trp53 tied to TagBFP2 expression (FIG. 2H). We tested this multi-miR-E construct and observed mRNA-level knockdown efficiency at around 80%, comparable to the originally reported efficiency (FIG. 2I). In agreement with the MADM findings, we observed the selective over-growth of TagBFP2+/Pdgfra+ OPCs, aligning with previous observations that LOF models based on Nf1 and Trp53 result in OPC-driven hyperplasia (FIG. 2J and FIG. 10a). Notably, the sibling EGFP+ population, which does not contain the miR-E's yielded a quantitatively smaller, mixed population of mostly astrocytic cells (FIG. 2J and data not shown). These genetically defined (i.e. EGFP+) sibling cells could serve as a useful control cell population in a manner akin to the wild-type cells in MADM GEMM systems. (MADM and MASTR allow rigorous, *Drosophila*-like deciphering of mutant cells but require de novo GEMM generation depending on the chromosomal location of GOIs. We also observed that the expression of three miR-Es did not prevent OB neurogenesis (FIG. 10B), which is counter to our previous findings using Hras, and Errb2, suggesting GOF and LOF mutations resulting in increased Ras/MAPK signaling may lead to subtly different cell fate alterations. Albeit with a small group of animals, we did not detect any malignancy 200 days post-EP, indicating that the complete ablation—rather than knockdown—of any one, two, or all of Nf1 P53 and Pten is likely required for highly penetrant, early-onset tumorigenesis. As confirmation of this, we used CRISPR/Cas9-based knockout of these suppressors. Notably, by EPing a combination of sgRNAs against Nf1, Trp53, and Pten along with SpCas9 and piggyBac-mediated EGFP labeling, we noted the formation of white matter associated, high grade, Olig2$^+$ tumors (FIG. 10d-e) in agreement with GEMM glioma models, the MADM glioma models and an in utero EP-based CRISPR model. Nevertheless, our miR-E studies demonstrate the usefulness of MADR in performing lineage tracing after single-copy, stable knockdown of target genes while providing for an internal "control" lineage (i.e. the EGFP+ Cre-recombined cells).

Generation of Focal Glioma Models Based on In Vivo MADR

Figure 13:
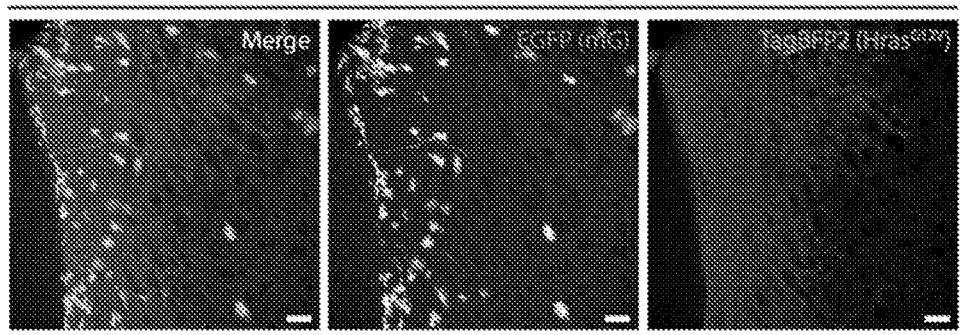
FIGS. 13A-13C depict examination of HrasG12V-recombined mTmG cells in the striatum in accordance with various embodiments of the present invention.
Figure 13:
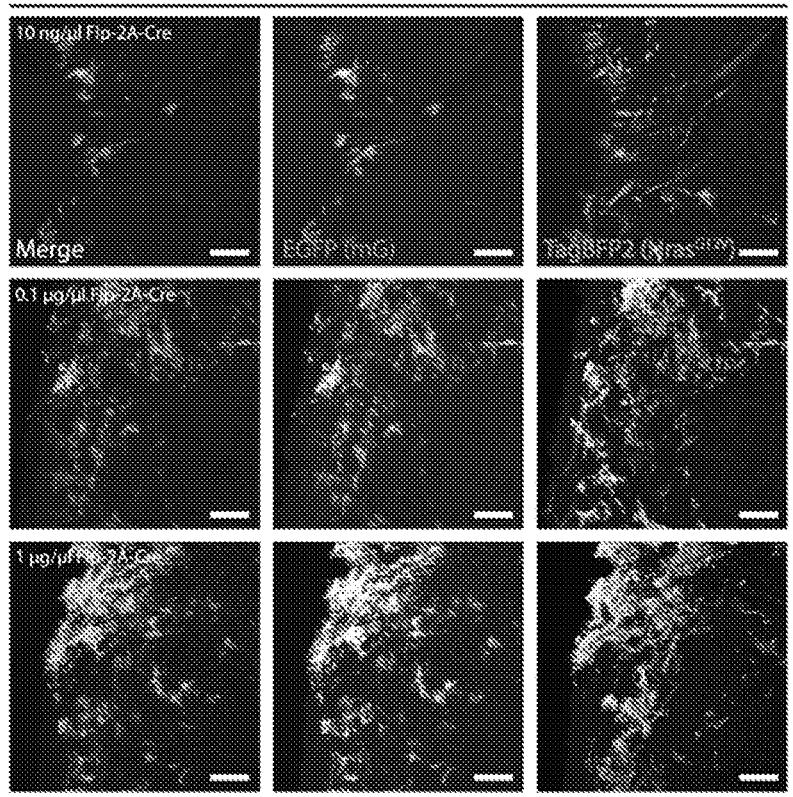
Figure 13:
Figure 13:

Viral and EP tumor models are increasingly employed to study developmental, evolutionary aspects of cancer in various tissue, but there are issues with various gene delivery methods. We reasoned that our method could be best suited for in vivo, autochthonous modeling of putative cancer driver genes, and for proof-of-principle, chose Hras$^{G12V}$, a highly-used activating oncogene. Histological analysis of growth dynamics in putatively single-copy heterozygous mice indicated that Hras$^{G12V}$ cells rapidly over-proliferated when compared with EGFP+ populations (FIG. 13A). Moreover, we reasoned that we might be able to distinguish between heterozygous and homozygous populations of cells by breeding the mTmG mice to homozygosity. Specifically, four possibilities could theoretically result after recombination or insertion and each would have a different combination of genetic markers (FIG. 2B). After a P2 EP, all of the homozygous mTmG EP-ed with Hras$^{G12V}$ rapidly developed glioma and reached terminal morbidity within 3-4 months (FIG. 2a; n=4). (Using the same oncogene driven by the CAG-promoter, we have previously shown that PB-EP of Hras$^{G12V}$ results in 100% penetrant glioma.) In homozygous mTmG mice, the MADR reaction was highly efficient even when using 10 ng/µl of plasmid (FIG. 13B). Interestingly, in our homozygous mTmG gliomas, blue-only cells (Rosa26$^{HrasG12V \times 2}$) occupied a bigger patch of tumor cross-section than cells expressing both blue and green (Rosa26$^{HrasG12V \times 1}$) (FIG. 2c, 7b). Previously, Hras$^{G12V}$ copy number has been shown to confer phenotypic differences, such as growth and apoptosis rates. Using PB-EP, we also observe that the brighter EGFP-tagged Hras$^{G12V}$ cells express phosphorylated Rb1 (pRb1) more than the dimmer EGFP+ cells (FIG. 13C). Similarly, most of the putatively homozygous Rosa26$^{HrasG12V \times 2}$ cells in mTmG mice EP-ed with Hras$^{G12V}$ seem to express pRb1, whereas the hemizygous Rosa26$^{HrasG12V \times 1}$ do not (FIG. 7b-7c). This data points to a possibility that the copy number of oncogenes can significantly alter the profile of resulting tumor populations, as previously observed using GEMMs.

Figure 11:
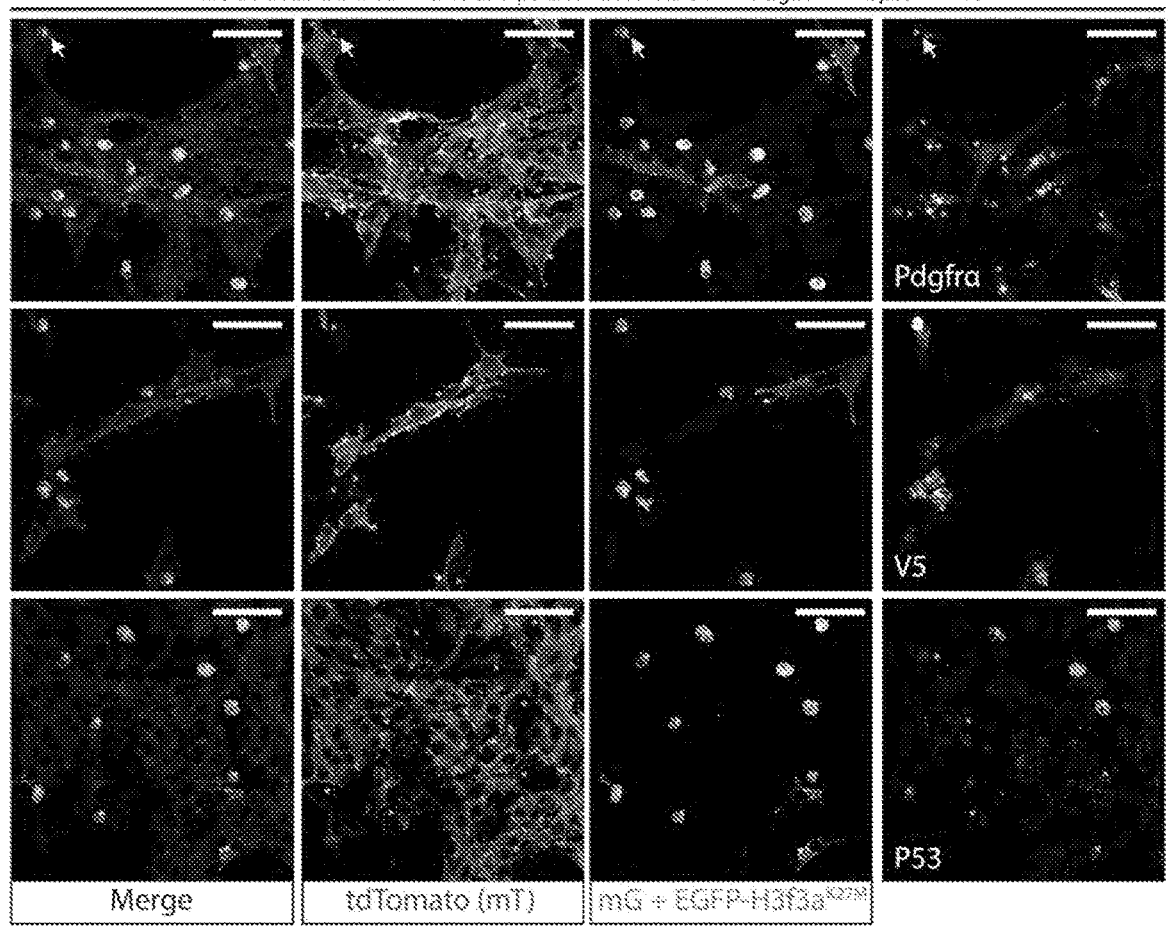
FIGS. 11A-11J depict confirmation of Pdgfra and V5-tagged Trp53 expression by in vitro and in vivo immunohistochemistry in accordance with various embodiments of the present invention.
Figure 11:
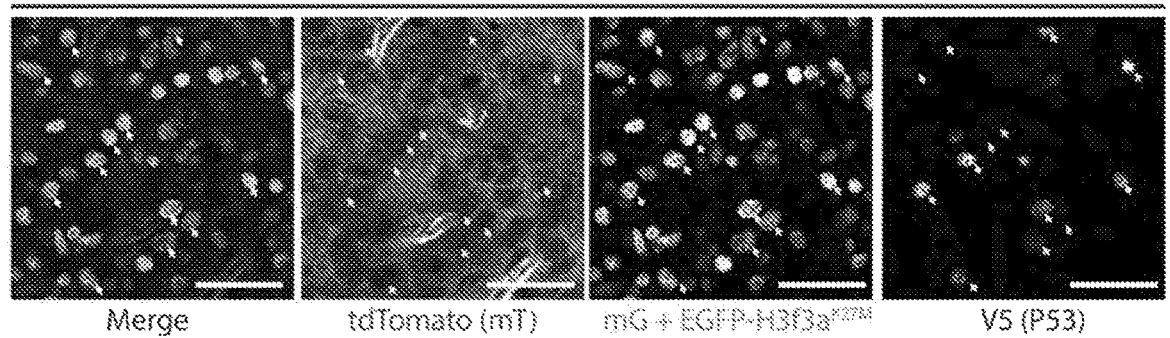
Figure 11:
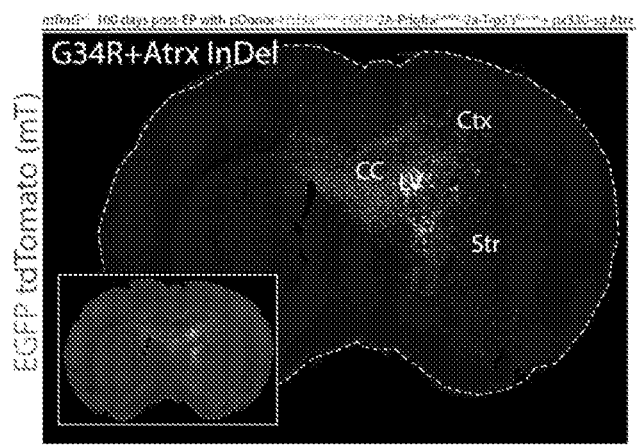
Figure 11:
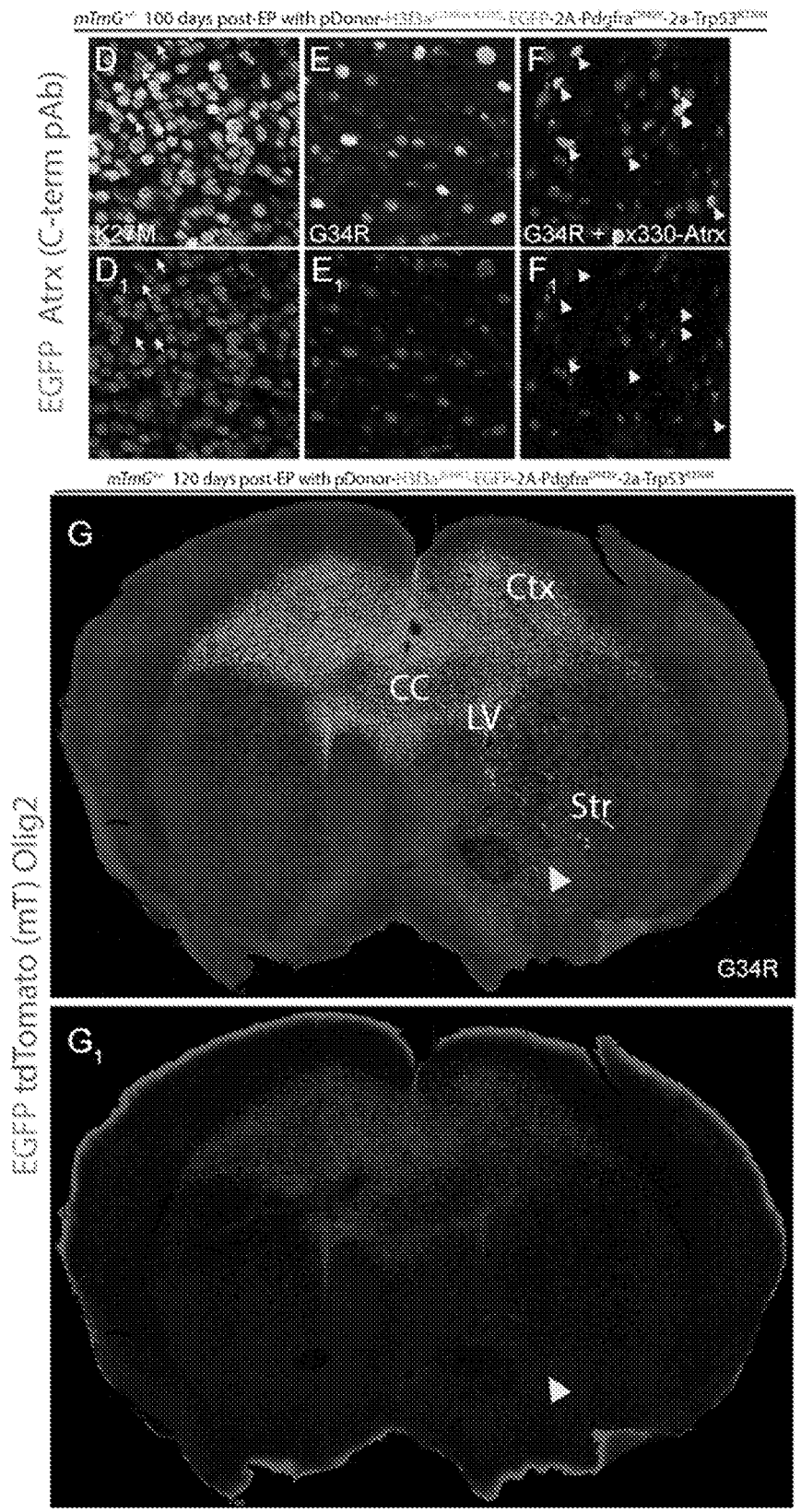
Figure 11:
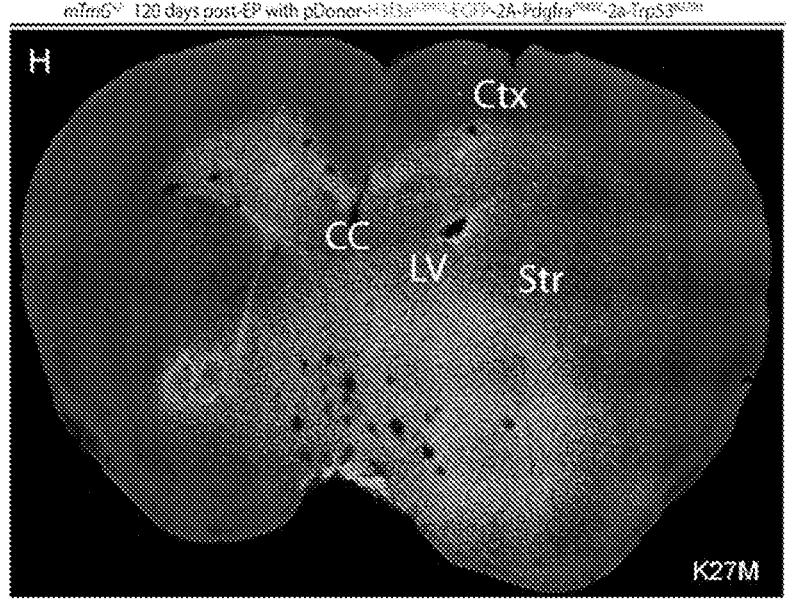
Figure 11:
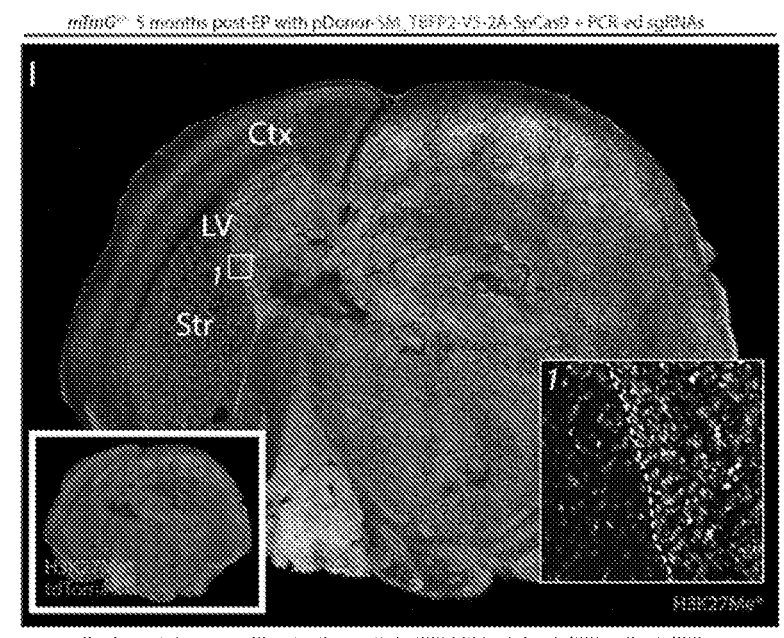
Figure 11:
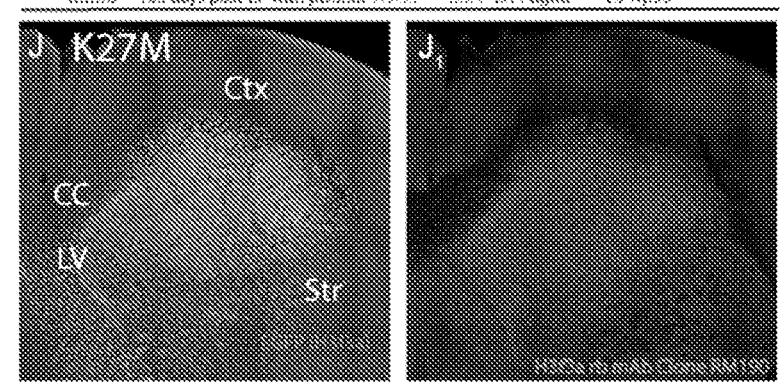
Figure 14:
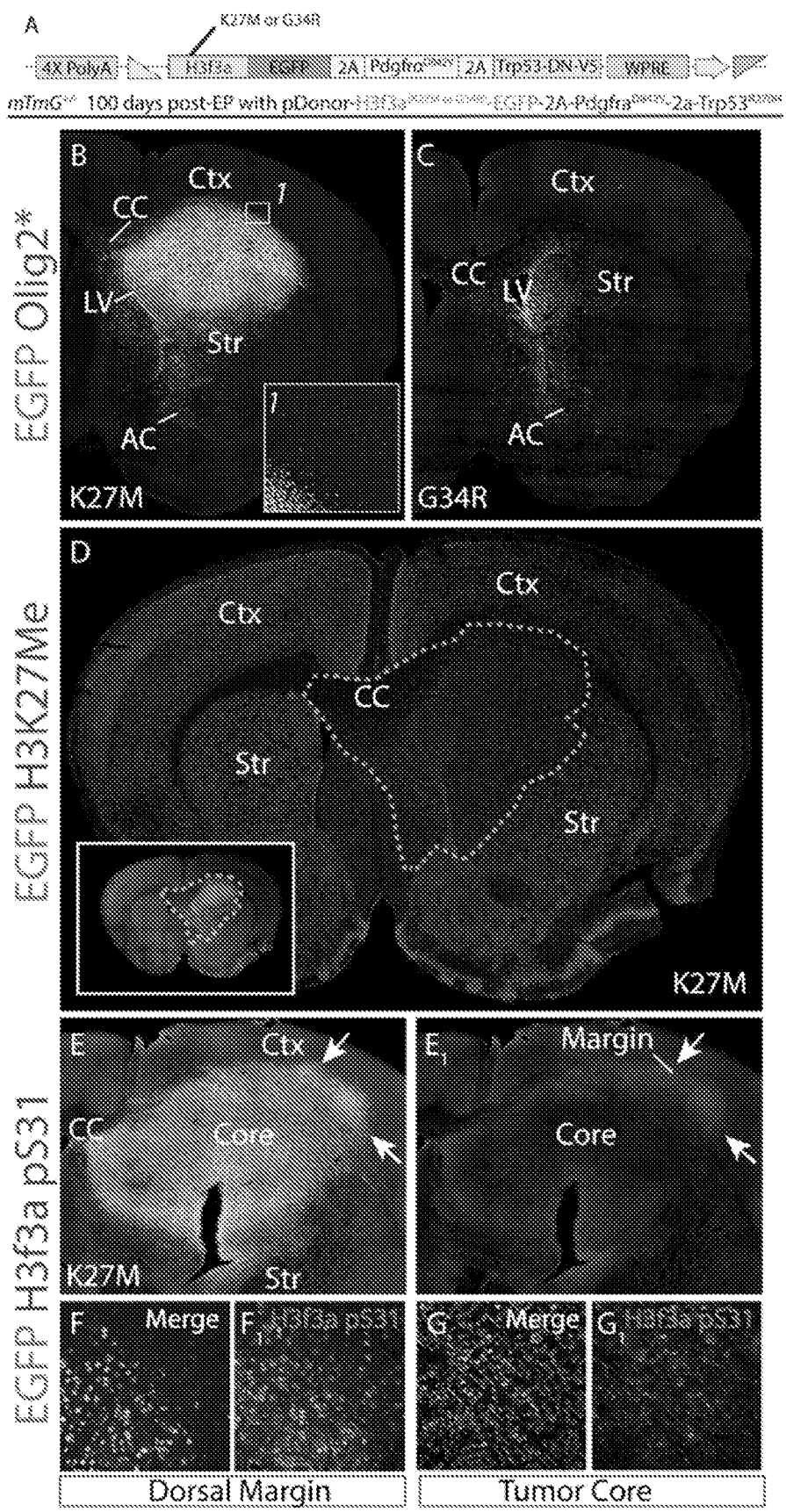
FIGS. 14A-14G show that generation of MADR glioma models utilizing recurrent mutations observed in pediatric GBM yields phenotypes consistent with human subtypes and gives insights into alterations H3f3a PTMs in accordance with various embodiments of the present invention.

A current unmet need in terms of mouse models of cancer is a higher throughput method of "personalized" tumor modeling. With the recent surge of knowledge about the putative driver mutations in cancer, there is a need for platforms that can rapidly and comprehensive model these mutations in vivo in a combinatorial manner. For example, recently, H3F3A, PDGFRA, and TRP53 were found to be recurrent in pediatric gliomas. Intriguingly, the H3F3A mutations were in two residues—K27 and G34. Notably, resulting patient tumors bearing either K27M or G34R/V mutations in H3F3A exhibit markedly different transcriptomes as well as clinical behaviors. In particular, patient K27M gliomas cluster along the midline and emerge earlier than G34R/V gliomas, which largely reside in the cerebral hemispheres. Nevertheless, H3F3A gliomas of both classes typically harbor TRP53 mutations and can exhibit PDGFRA activating mutations. To model these pediatric tumors in mice, we generated a cassette for co-expression of H3f3a mutations (tagged to EGFP), an activated Pdgfra (D842V), and mutant Trp53 (R270H) (FIG. 14). First, we checked for appropriate expression of H3f3a, Pdgfra, and Trp53 by immunohistochemistry in vivo and in vitro and noted coincident expression of all proteins (FIG. 11A-B). Next, we introduced these plasmids by postnatal EP into littermates. Importantly, the electrodes were swept to EP both cortical and striatal VZs to allow for possible tumor formation from both progenitor zones. Fascinatingly, and seemingly in agreement with the clinical presentation of these tumors, K27M-bearing littermates exhibited midline gliomas by P100 (FIG. 14B), whereas similarly-treated G34R-bearing littermates mostly displayed diffuse glial hyperplasias and very rare, small tumors (FIG. 14C, arrowhead). Because G34R mutations often present with ATRX mutations in the second half of the coding sequence, we used CRISPR/CAS9 to introduce InDels mimicking these naturally-occurring mutations. After co-introduction of an SpCas9-expressing plasmid with an sgRNA targeting ATRX along with the G34R-containing co-expression cassette, no gross change was seen in the behavior of G34R glial cells in terms of proclivity for tumor formation at P100 (FIG. 11C). (A previously-validated antibody recognizing the c terminus of Atrx demonstrated that >90% of K27M cells and 100% of G34R MADR cells expressed full length Atrx, while >95% of G34R cells with CRISPR/Cas9-targeting of Atrx failed to show Atrx antibody labeling (FIG. 11D-E).) Notably, at 120 days post-EP, G34R tumors were observed and localized to the cortex and underlying callosum despite equal targeting of the striatal VZ (and coincided hyperplasia of some of these cells; FIG. 11G). Interestingly, Olig2 signal was significantly more prominent in the dorsal regions, suggesting a cell fate discrepancy between tumor and hyperplasia (FIG. 11 $G_1$). At this same 120 day time point, K27M tumors predominantly localized to the sub-cortical structures but cells could be observed in the white matter tracts with a minor amount of cells in the deeper cortical layers (FIG. 11H). These findings indicate that the K27 and G34 residues are sufficient to significantly regulate the time and location of onset of these glioma subtypes despite the coincident presence of the potent Pdgfra and Trp53 mutations. Further, somatic Atrx mutations do not appear to be a rate-limiting step for tumor formation in G34R tumors.

Mechanistically, it is thought that K27M mutations lead to hypomethylation at this residue. In fact, given the intrinsic ability of MADR to lineage trace tumor cells, we were able to confirm the hypomethylation of K27M mutant cells by K27Me antibody (FIG. 14D). (This was not simply an artifact of tumor growth as CRISPR/Cas9-mediated knockout of Nf1/Trp53 led to the formation of glioma that was hypermethylated (FIG. 11I).) Recently, it was found that phosphorylation of Serine 31 (heretofore phosphoSer31), which lies between K27 and G34, is important for Trp53-mediated cell cycle arrest and that this might lead to a short-circuiting of the aneuploidy failsafe. Again using our ability to lineage trace tumor cells, we noted a striking pattern of phosphoSer31, whereby it was found at the tumor margins but not in the core (FIG. 14E). This was confirmed by high magnification confocal z stacks (FIG. 14F-G). Further, a monoclonal antibody to H3f3a confirmed the presence of the protein throughout the tumor (FIG. 11J). Though this staining pattern is highly suggestive of a potential role in tumor dissemination, further studies will be needed to investigate whether this phosphorylation is functionally important for tumor dynamics. Taken together, the ability to easily and unambiguously observe such post-translation changes in a tumor cell autonomous manner in vivo holds great promise for the future investigations of disease pathomechanisms in these and other cancers.

Figure 15:
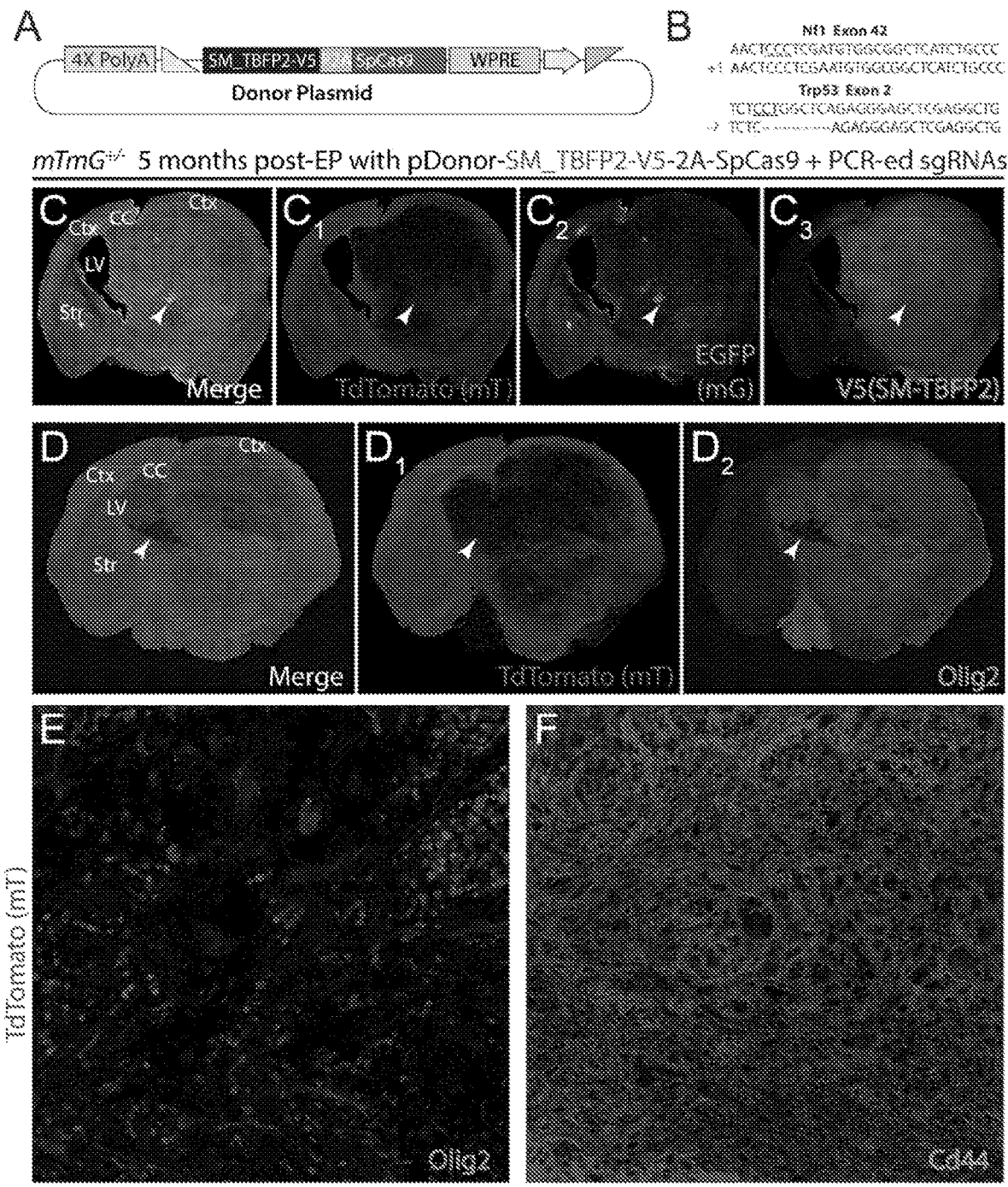
FIGS. 15A-15H show that rapid generation of somatic mosaics using in vivo MADR-incorporated Cas9 and PCR-derived sgRNAs allows for interrogation of transdifferentiation within glioma in accordance with various embodiments of the present invention.
Figure 15:
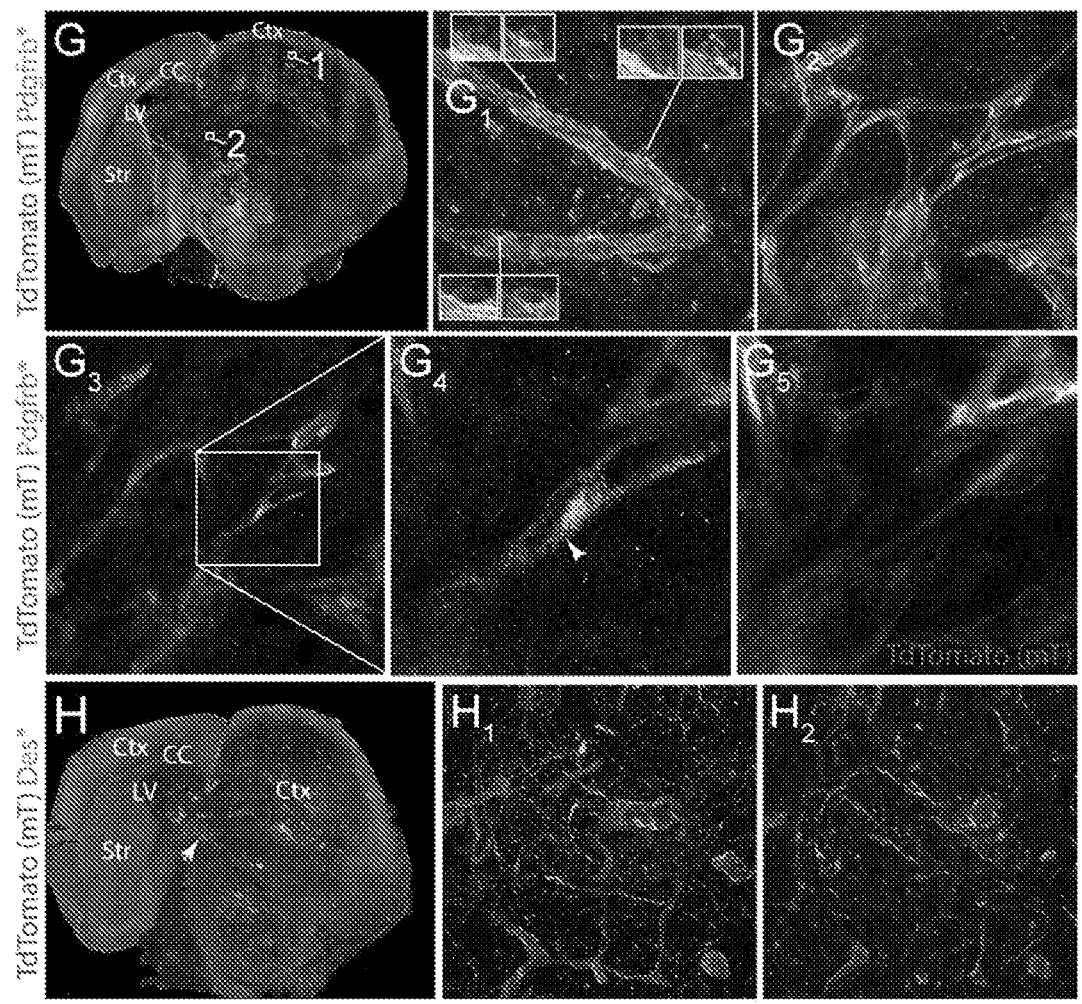

Lineage Tracing CRISPR/Cas9 Induced MADR MAX Glioma Models Reveals Tumor to Pericyte Transdifferentiation Recently, CRISPR/Cas9 has been demonstrated to be highly efficacious for the mutation of genes in vivo using EP. However, a shortcoming of these studies is a definitive way to lineage trace modified cells. To address this issue, we created a SM_BFP2-P2a-SpCas9-containing donor plasmid to simultaneously label and mutate cells, enabling faithful tracing of mutant cells in vivo (FIG. 15A). Given our aforementioned findings with the tandem miR-E's and the Cas9-mediated knockout of Nf1, Trp53, and Pten, we used these same PCR-ed sgRNAs to target Nf1 and Trp53. Successful targeting in EPed cells was confirmed in tumor population gDNA by sequencing (FIG. 15B). At roughly 5 months we observed terminal morbidity in EPed animals. Pathological analysis led to the diagnosis of glioblastoma multiforme, principally due to the presence of necrosis in the tumor. Immunohistochemically, we observed that the tumor was largely devoid of TdTomato-labeled populations with the exception of vasculature (FIG. 15C-$C_1$). A small EGFP population was observed near where the original targeting site was expected to reside (FIG. 15C, $C_2$; arrowhead). However, the tumor was demarcated by MADR MAX SM_BFP-V5 labeled cells, which had overgrown the hemisphere (FIG. 15C, $C_3$). Most of this volume was filled with Olig2+ populations though regions lacking signal were observed (FIG. 15; arrowhead; 15E). As Olig2 is a marker of proneural glioma subtypes, which we and others have observed to precede mesenchymal evolution, we assessed whether this might be a site of tumor evolution by staining for the mesenchymal marker, CD44. Notably, CD44 was found throughout the tumor but was enriched in this Olig2-diminished region (FIG. 15E-F and data not shown). Due to the prominence of the TdTomato vasculature and the ability of the SM_BFP-V5 to discriminate tumor cell lineages, a conspicuous population of V5-tagged perivascular cells stood out from the other populations (FIG. 16A; arrows). Given the location and morphology of these cells along with our ability to genetically discriminate tumor cells from stroma with genetic markers; we revisited the current controversy regarding the transdifferentiation of glioma cells. Specifically, several groups had indicated that glioma cells could transdifferentiate into endothelial. This was contested by findings that the transdifferentiation was instead into pericytes. Other groups have found a lack of evidence for either despite considerable investigation. In examining the co-localization of Pecam1, a bona fide marker of endothelial cells, with TdTomato, we noted that virtually all Pecam1+ cells were co-labeled, suggesting that the vasculature was not tumor derived (FIG. 16B). However, we noted extremely rare Pecam1+/TdTomato- signals, most of which appear to be debris given the small size (<5 μm) and a handful of profiles which were the size of normal endothelial cells (FIG. 16C-D). However, vessel-associated cells were not found and the numbers of these putative cells were not amenable to systematic investigation (FIG. 16C-D). Conversely, using both Pdgfrb and Des (aka Desmin), well-validated pericyte markers, we were able to observe discrete locations in and around the aforementioned Olig2-/Cd44+ sites (in roughly adjacent sections to the regions depicted by the arrowhead in FIG. 15D) that exhibited positivity for either pericyte marker in the absence of TdTomato (FIG. 15G-H). Despite antibody amplification of TdTomato and artifactually overexposing the TdTomato signal in these regions, we did not see co-localization of the TdTomato and Des in some pericytes (FIG. 16E). However, in most regions of the tumor—specifically the Olig2-enriched regions—these pericyte markers were found to strictly co-localize with TdTomato membranes, suggesting that this transdifferentiation was not widespread in proneural subtype dominated regions (FIG. 16F). Thus, using our novel autochthonous models, which allow for unambiguous genetic labeling of multiple populations in vivo, we provide evidence for focal transdifferentiation of tumor cells into pericytes in GBM. This suggests that transdifferentiation of glioma cells into pericytes may correlate with the heterogeneous evolution of glioma, including from proneural into mesenchymal subtypes.

With the recent surge of putative driver mutations, there is a need for platforms that can rapidly and comprehensive model these mutations in vivo in a combinatorial manner. Recently, H3f3a, Pdgfra, and Trp53 were found to be recurrent in pediatric gliomas. We demonstrate that EP of two donor plasmids carrying different combinations of these mutations result in proliferating hyperplasias by P50 (FIG. 2f,g). We checked for expression of H3f3a, Pdgfra, and Trp53 by immunohistochemistry in vivo and in vitro (FIG. 2g and FIG. 11a,b).

We demonstrated that dRMCE-mediated somatic transgenesis in vivo is a highly robust, cost-effective method for creating numerous somatic mosaics using one mouse line. Specifically, dRMCE has been utilized recently in vitro but suffers from relatively low efficiency of insertions, thus requiring antibiotic selection of clonal cell lines and rigorous validation of individual cell lines with molecular biological methods (PCR, southern blot, etc.). Here we demonstrate that we can achieve roughly 90% expression of transgenes in vivo with RMCE by careful plasmid design, by titration of the constituent plasmid elements and, by utilizing a "safe-landing site" (e.g., the ROSA26 locus for various embodiments described herein). This allows for consistent, rigorous, and facile investigation of single or dual copy transgene expression. By comparison, episomal and transposon mediated insertion often leads to the supraphysiological expression from tens or hundreds of copies of the given transgene. Moreover, episomal transgenes will more often dilute in proliferating lineages and transpon-based methods will cause cassette "hopping" in the presence of transposases, potentially disrupting endogenous gene function, including tumor suppressors, cell cycle genes, etc. Further, through the use of the mt/mg reporters to delineate recombinase events, by titrating plasmid constituents and by using multiple donor plasmids, one can track multiple independent lineages.

Figure 12:
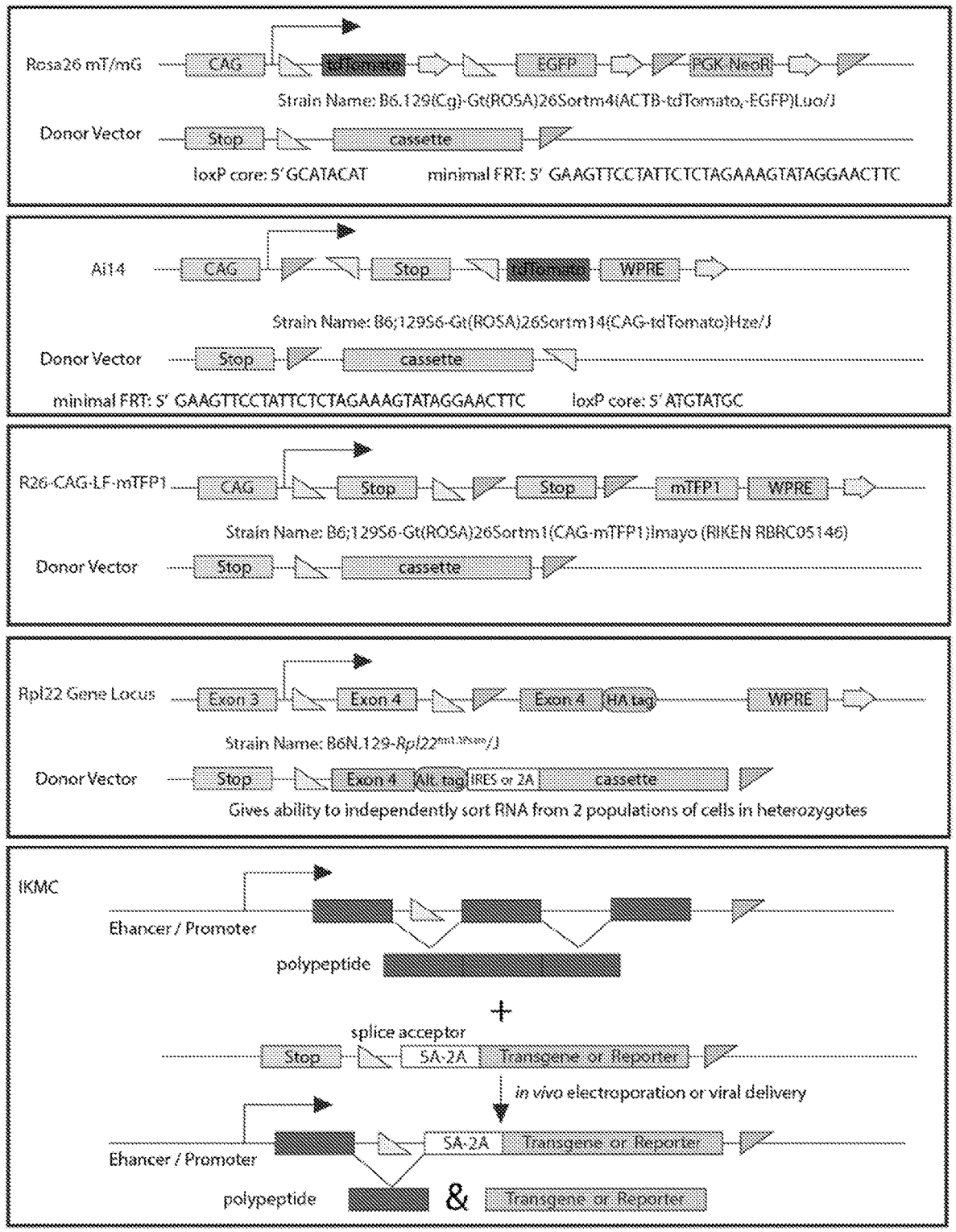
FIG. 12 depicts alternative reporter mice amenable to in vivo MADR or MADR MAX, and extension of the method to Ribotrap and IKMC repository mouse lines with gene-trap alleles in accordance with various embodiments of the present invention. There are existing CAG-based reporter mice that are similar to mTmG mice in construction and compatible with in vivo MADR to achieve mutant lineage tracing studies or orthogonal RNA isolation using Ribotrap heterozygotes. Additionally, this method can extend to thousands of gene-trap mice that, as an example, flank loxP and FRT around important exons. in vivo MADR at such loci would enable 1) lineage tracing of heterozygous/homozygous null cells at the locus, as well as 2) swapping the locus with a transgene. Sequences in the figure—top panel: loxP core GCATACAT (SEQ ID NO:12); minimal FRT: GAAGTTCCTATTCTCTAGAAAGTATAGGAACTTC (SEQ ID: 13); second panel: minimal FRT: GAAGTTCC-TATTCTCTAGAAAGTATAGGAACTTC (SEQ ID: 13); loxP core: ATAGTATGC (SEQ ID: 14).

We demonstrated the ability to combine flexibly two broad modes (GOF/LOF) of tumor mutations. This strategy can be employed with any off-the-shelf GEMM harboring dual recombinase sites (e.g., Ail4, R26-CAG-LF-mTFP1, and IKMC mice), allowing for the definitive assessment of GOF and LOF protein functions in vivo at a defined dosage (FIG. 12). This strategy can also be extended to other organs, such as lungs, breast, and many more, in conjunction with viral vectors and other gene delivery methods.

Our in vivo MADR efficiency experiment indicates that diluting the concentration of donor construct possibly mimics single-substrate-based recombination reactions that occur in double-transgenic GEMMs with floxed loci and Cre-recombinase (FIG. 1f). We demonstrated the potential to expeditiously and flexibly combine two broad modes (GOF/LOF) of tumor mutations. All in all, we have introduced a new technique to produce stable, defined copy number, somatic mosaicism in mice with EP. The intrinsic features of MADR compared favorably with existing methods for in vivo mouse genetic manipulation using other methods (Table 2). Going forward, if the desired donor element is sufficiently small in size, non-integrating viral vectors can be used, expanding the number of tissues that can be targeted.

TABLE 2

| Method | GEMM | Standard EP | Transposition-mediated EP | Virus | MADR |
|---|---|---|---|---|---|
| Time for engineering and generation | Months | ~2 weeks per plasmid | ~2 weeks per plasmid | >4-6 weeks | ~2 weeks per plasmid |
| Copy number | 1-2 per knock-in | Highly Variable | Highly Variable | Variable but likely less than EP | 1-2 depending on zygosity of recipient |
| Breeding | More complex for conditional alleles | Not Necessary | Not Necessary | Only Necessary for RCAS/Tva | 1 line per targeted stain |
| Stability of Expression | Generally stable depending on locus silencing | Prone to dilution and/or silencing | Prone to silencing and insertional effects | Prone to silencing and insertional effects | Generally stable depending on locus silencing |
| Payload | Limited by targeting construct* | Typically governed by plasmid limits* | Typically governed by plasmid limits* | Limited to viral payloads | Typically governed by plasmid limits* |
| Focality | Depends on cis regulatory elements | Focality depends on electrode orientation | Focality depends on electrode orientation | Diffusion pattern unidirectional from injection site | Focality depends on electrode orientation |

*BAC DNA can be utilized

New MADR EP Toolkit

Transposons, such as PB and Sleeping Beauty, are increasingly used in combination with EP to produce stable somatic trangenics with several reports utilizing these techniques in recent years. Transposons are extremely attractive tools because they allow long-term developmental studies and also in vivo tumor generation. Our new method overcomes transposon system's two major problems: random genomic insertions and copy number variability. Notch signaling is one key example of gene-dosage-sensitive molecular pathways. Additionally, several other cell-fate determinants have been shown to result in dramatically differential phenotypes based on their expression levels. For example, high Nfia expression in glial progenitors favor their differentiation into astrocytes, while low expression is observed in cells that become oligodendrocytes, and in another example, higher Fezf2 expression induces the NSC quiescence in the VZ/SVZ by upregulating Notch signaling effectors. Our method can be used for rapidly assessing such pathways in vivo. Using one-copy vs. two-copy comparison paradigm shown in this report, such nuclear factors can be investigated in one mouse with natural intra-section control cells. Our in vivo MADR is extensible and relatively inexpensive when compared with GEMM engineering. Moreover, given the fact that the postnatal EP procedure is rapid (~35 minutes per litter of animals) and requires no invasive surgery, this methodology can be easily adopted by many labs.

Extensibility of MADR to Existing GEMMs

Figure 16:
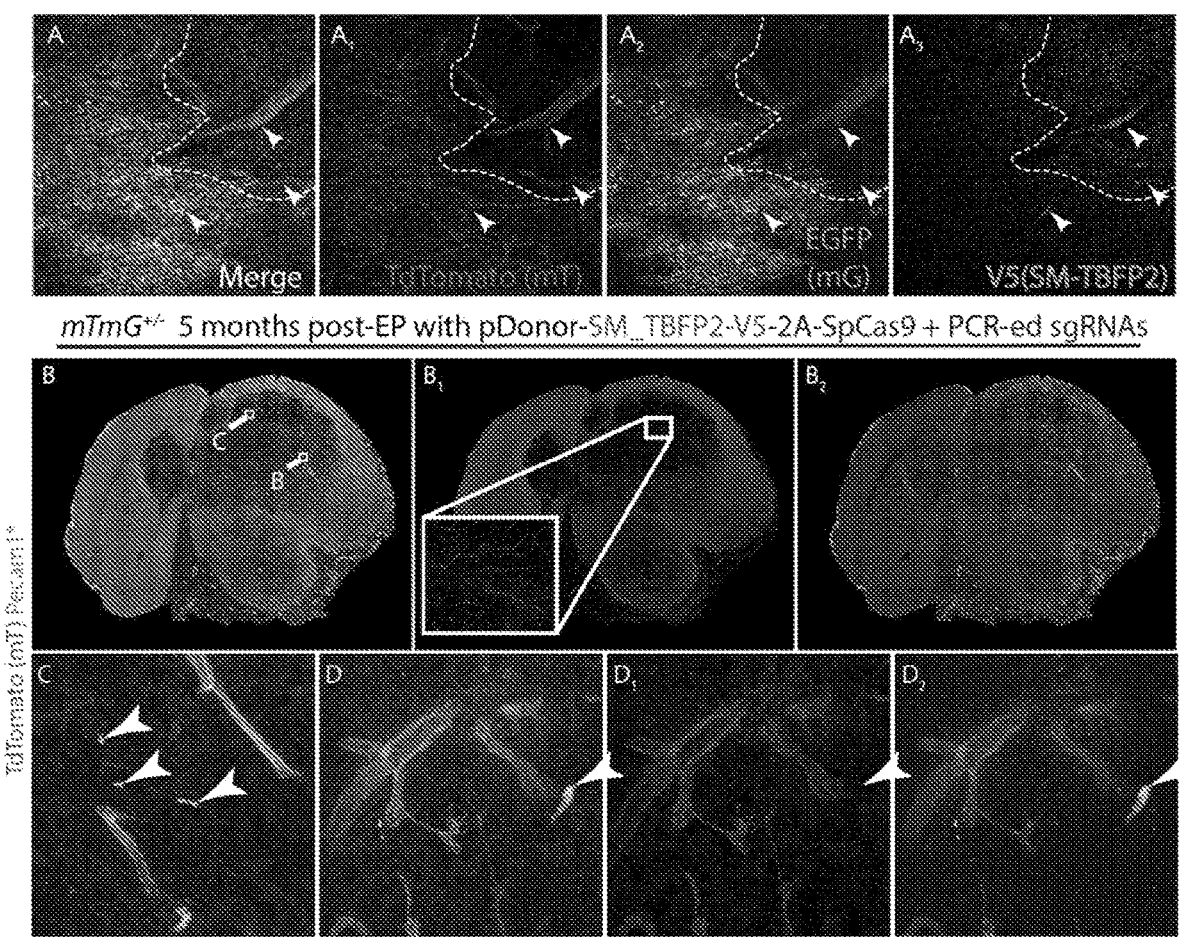
FIGS. 16A-16F depict investigation of transdifferentiation in MADR glioma in accordance with various embodiments of the present invention.
Figure 16:
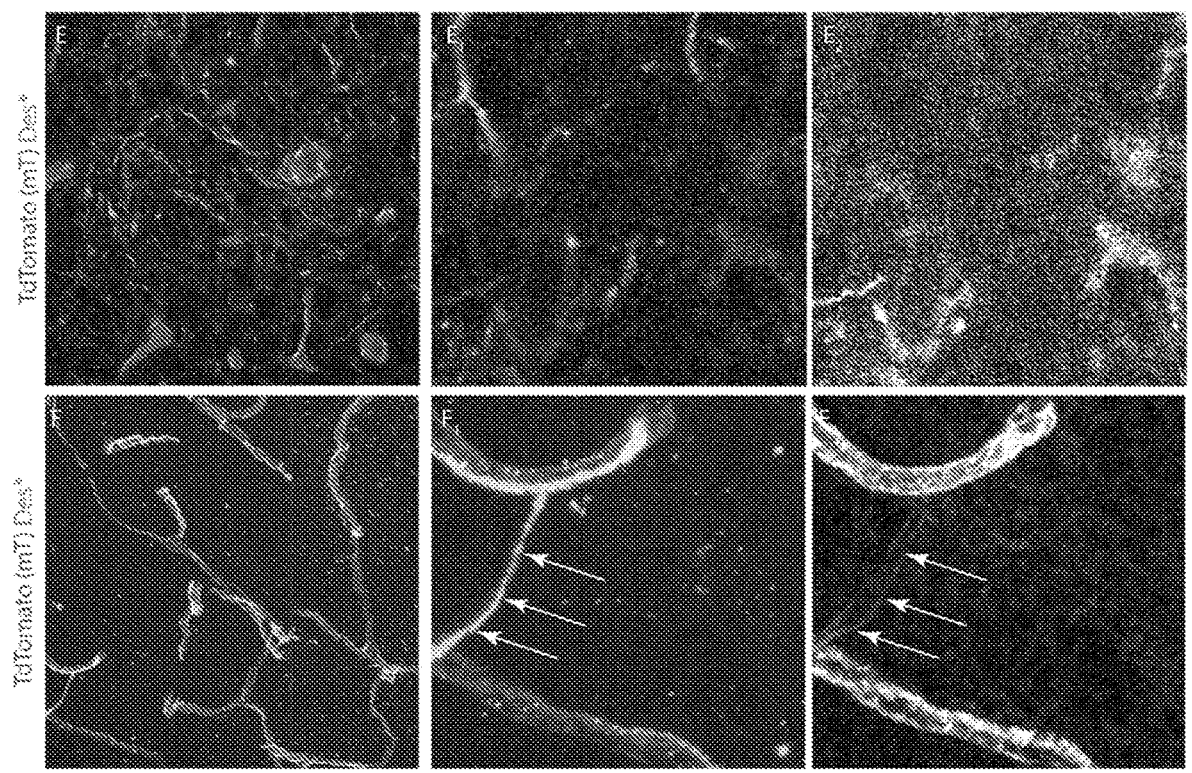

This strategy can be employed with any off-the-shelf GEMM harboring dual recombinase sites (e.g. Ai14, R26-CAG-LF-mTFP1, Ribotag, and IKMC mice), allowing for the definitive assessment of GOF and LOF protein functions in vivo at a defined dosage (FIG. 16). There are thousands of transgenic mice that already harbor loxP and FRT sites around loci of interest. Like Rosa26$^{mTmG}$, Ai14 is another widely employed reporter mouse line that are typically crossbred with recombinase-expressing transgenic mice. By appropriately orienting the recombinase recognition sites, as indicated in FIG. 16, donor plasmids can be created for use in Ai14 mice. Ribotag use Cre recombination to swap an untagged Rpl22 Exon 4 with an HA-tagged variant for affinity immunoprecipitation of Cre expression-defined mRNA. With MADR, an alternate tag can be inserted with additional orthogonal elements to allow for simultaneous orthogonal mRNA purification using sequential immunoprecipitation for the tags. In addition, one can create an ORF that begins with a splice acceptor and use this construct to investigate the effects of substituting transgenes under foreign cis-regulatory environments (FIG. 16). At the same time, a donor plasmid with a fluorescent reporter can be simply electroporated (with Flp and Cre) to enable lineage-tracing from a focal point without the need for Cre-expressing mice in various transgenic mice that flank important loci with loxP and FRT sites.

Because our method requires two different recombinases, one can also drive the expression of these recombinases with different combinations of promoters to restrict the types of cells that are recombined. For example, this method can be used to compare and contrast the fate-mapping of lineages that arise from discrete stem and progenitor subsets by using cell type-specific Flp/Cre expression. Finally, there is in vivo MADR with large-cargo bacterial artificial chromosomes (BAC). A donor plasmid harboring large chunks of genomic fragments driving the expression of fluorescent reporter or recombinases, such as vCre or sCRE, can be created with loxP and FRT sites added on each end. Then, EP can deliver this large fragment at limiting dilutions into the genome in combination with additional plasmids carrying vCre/sCre-activatable reporters. This type of study would effectively enable GEMM-like, higher-order lineage tracing studies.

Next generation sequencing has exponentially increased our understanding of the genomic and transcriptomic changes that occur in tumorigenesis. However, with the catalogue of recurrent somatic mutations in tumors continuing to grow, an emerging problem is to separate tumor-promoting driver mutations from passenger mutations. Further, it is now increasingly appreciated that similarly histologically classified tumors can often have disparate genetic underpinnings that create notably different tumor phenotypes (e.g., K27M vs. G34R tumors). GEMMS have been the critical for the understanding of glioma development. In particular, the elegant MADM methodology has provided unique insights into the tumor cell of origin and potential treatments. We show proof of principle for using MADR as a platform for rapid 'personalized' modeling of pediatric GBM. By combining MADR GOF transgenesis, and CRISPR/Cas9 LOF manipulations, it is possible for a small lab to generate the plasmid reagents necessary to cover the spectrum—and, thus, possible combinations—of mutations for most tumor types.

Our findings therefore establish in vivo MADR as a robust methodology for stable mosaic analysis, one which overcomes many of the inherent drawbacks in viral, GEMM, EP, and transposon-based approaches. Additionally, this genetic framework is adaptable to the thousands of strains of mice engineered with dual recombinase recognition sites. Thus, these tools promise to allow for efficient, higher throughput investigation of gene function in development and disease.

Accordingly, various embodiments of the present invention are based, at least in part, on these findings.

Donor Vectors

Various embodiments of the present invention provide for a promoter-less donor vector, comprising: a polyadenylation signal or transcription stop element upstream from a transgene or RNA; the transgene or RNA; and paired recombinase recognition sites.

In various embodiments, the promoter-less donor vector further comprises a post-transcriptional regulatory element.

In various embodiments, the promoter-less donor vector further comprises a polyadenylation signal downstream from the transgene or RNA.

In various embodiments, the promoter-less donor vector comprises PGK polyadenylation signal (pA); trimerized SV40 pA; a transgene or RNA; loxP; flippase recognition target (FRT); a woodchuck hepatitis virus post-transcriptional regulatory element (WPRE); and a rabbit beta-globin pA.

Various embodiments of the present invention provide for a promoter-less donor vector, comprising: a transcription stop element upstream from a transgene or RNA; paired recombinase recognition sites; rtTA-V10; the transgene or RNA; and TRE-Bi. In various embodiments, the promoter-less donor vector further comprises a post-transcriptional regulatory element. In various embodiments, the promoter-less donor vector further comprises a gene encoding puromycin.

In various embodiments the promoter-less donor vector, comprises: a transcription stop element upstream from a transgene or RNA; loxP; rtTA-V10; the transgene or RNA; TRE-Bi; and flippase recognition target (FRT). In various embodiments, the promoter-less donor vector further comprises a post-transcriptional regulatory element. In various embodiments, the promoter-less donor vector further comprises a gene encoding puromycin Various embodiments of the present invention provide for a promoter-less donor vector, comprising: a transcription stop element upstream from a transgene or RNA; paired recombinase recognition sites; rtTA-V10; the transgene or RNA; and TRE-Bi-Dll1. In various embodiments, the promoter-less donor vector further comprises a post-transcriptional regulatory element. In various embodiments, the promoter-less donor vector further comprises a gene encoding puromycin.

In various embodiments, the promoter-less donor vector comprises: a transcription stop element upstream from a transgene or RNA; loxP; rtTA-V10; the transgene or RNA; TRE-Bi-Dll1; and flippase recognition target (FRT). In various embodiments, the promoter-less donor vector further comprises a gene encoding puromycin.

The orientation of the paired recombinase sites are dictated by the engineered locus in the transgenic animal (i.e., the recombinase sites will exactly mimic the outer pair of recombinase sites if the transgene is to be inserted in the 'sense' direction of the upstream promoter). Accordingly, in various embodiments, the paired recombinase recognition sites are in the correct orientation. In various embodiments, the loxP is not in an inverted orientation.

In various embodiments, the paired recombinase recognition sites are loxP and flippase recognition target (FRT), and the recombinases are cre and flp. Examples of Flp include flpE and flpO.

Other examples of recombinases (and sites) include but are not limited to VCre (Vlox and derivatives), SCre (Slox and derivatives), Dre (Rox and derivatives), and phiC31 (attb).

In various embodiments, the RNA is siRNA, shRNA, or sgRNA.

In various embodiments, the transgene or the RNA comprises disease associated mutations. In various embodiments, the transgene or the RNA comprises a gain-of-function (GOF) mutation. In various embodiments, the transgene or the RNA comprises a loss-of-function (LOF) mutation.

Examples of transgenes include but are not limited to oncogenic gain-of-function mutations, including Ras, H3f3a, Pdgfra, Trp53 point mutations, Idh1. Examples of RNAs (shRNA and sgRNA) include but are not limited to tumor suppressor targets such as Trp53, Nf1, Atrx, or Pten.

Examples of post-transcriptional regulatory element include but are not limited to Hepatitis B virus post-transcriptional regulatory element (HPRE) and Woodchuck Hepatitis virus post-transcriptional regulatory element (WPRE).

In various embodiments, the promoter-less donor vectors describe above and below further comprise a gene encoding an antibiotic. In various embodiments, the promoter-less donor vector further comprises a gene encoding puromycin, or eukaryotic alternatives (kanomycin, blasticidin, etc.). In various embodiments, the promoter-less donor vector described above and below further comprises a gene encoding a doxycycline-regulated transactivator or CRISPR/Cas based variant (e.g., SpCas9 or Cpf1) for DNA cleavage, gene activation (Crispra), or gene repression (Crispri) when paired with an sgRNA.

In various embodiments, the promoter-less donor vectors described above and below further comprises a gene encoding one or more spaghetti monster fluorescent proteins (SM_FPs). In various embodiments, the one or more SM_FPs are each different SM_FPs. In various embodiments, the one or more SM_FPs are four different SM_FPs.

In various embodiments, the promoter-less donor vector further comprises a gene encoding one or more epitope tags. For example, 2, 3, 4, 5, 6, 7 8, 9, 10, 11, 12, 13, 14, or 15 epitope tags. The epitope tags may be the repeats or different tags. In various embodiments, the epitope tag is an HA tag, Myc tag, V5 tag, or Flag tag.

In various embodiments, the promoter-less donor vector comprises a large-cargo bacterial artificial chromosomes (BAC).

Systems

Various embodiments of the present invention provide for a system for use in in vivo dual recombinase-mediated cassette exchange.

In various embodiments, the system comprises: a promoter-less donor vector as disclosed herein; and one expression vector, comprising two genes encoding recombinases specific to the paired recombinase recognition sites.

In various embodiments, the system, comprises: a promoter-less donor vector as disclosed herein; and two expression vectors, the first expression vector comprising a first gene encoding a first recombinase that is specific to one of the paired recombinase recognition sites, and the second expression vector comprising a second gene encoding a second recombinase that is specific to the other of the paired recombinase recognition sites.

In various embodiments, the system, comprises: a promoter-less donor vector, comprising a polyadenylation signal or transcription stop element upstream from a transgene or RNA, the transgene or RNA, and paired recombinase recognition sites; and one expression vector, comprising two genes encoding recombinases specific to the paired recombinase recognition sites.

In various embodiments, the system, comprises: a promoter-less donor vector, comprising a polyadenylation signal or transcription stop element upstream from a transgene or RNA, the transgene or RNA, and paired recombinase recognition sites; and two expression vectors, the first expression vector comprising a first gene encoding a first recombinase that is specific to one of the paired recombinase recognition sites, and the second expression vector comprising a second gene encoding a second recombinase that is specific to the other of the paired recombinase recognition sites.

In various embodiments, the promoter-less donor vector further comprises a post-transcriptional regulatory element. In various embodiments, the promoter-less donor vector further comprises a polyadenylation signal downstream from the transgene or RNA.

In various embodiments, the promoter-less donor vector comprises: PGK polyadenylation signal (pA); trimerized SV40 pA; a transgene or RNA; loxP; flippase recognition target (FRT); a rabbit beta-globin pA; and a woodchuck hepatitis virus post-transcriptional regulatory element (WPRE).

The orientation of the paired recombinase sites are dictated by the engineered locus in the transgenic animal (i.e., the recombinase sites will exactly mimic the outer pair of recombinase sites if the transgene is to be inserted in the 'sense' direction of the upstream promoter). Accordingly, in various embodiments, the paired recombinase recognition sites are in the correct orientation. In various embodiments, the loxP is not in an inverted orientation.

In various embodiments, the paired recombinase recognition sites are loxP and flippase recognition target (FRT), and the recombinases are cre and flp. Examples of Flp include flpE and flpO.

Other examples of recombinases (and sites) include but are not limited to VCre (Vlox and derivatives), SCre (Slox and derivatives), Dre (Rox and derivatives), and phiC31 (attb).

In various embodiments, the RNA is siRNA, shRNA, or sgRNA.

In various embodiments, the transgene or the RNA comprises disease associated mutations. In various embodiments, the transgene or the RNA comprises a gain-of-function (GOF) mutation. In various embodiments, the transgene or the RNA comprises a loss-of-function (LOF) mutation.

Examples of transgenes include but are not limited to oncogenic gain-of-function mutations, including Ras, H3f3a, Pdgfra, Trp53 point mutations, Idh1. Examples of RNAs (shRNA and sgRNA) include but are not limited to tumor suppressor targets such as Trp53, Nf1, Atrx, or Pten.

Examples of post-transcriptional regulatory element include but are not limited to Hepatitis B virus post-transcriptional regulatory element (HPRE) and Woodchuck Hepatitis virus post-transcriptional regulatory element (WPRE).

In various embodiments, the promoter-less donor vectors describe above and below further comprise a gene encoding an antibiotic. In various embodiments, the promoter-less donor vector further comprises a gene encoding puromycin, or eukaryotic alternatives (kanomycin, blasticidin, etc.). In various embodiments, the promoter-less donor vector described above and below further comprises a gene encoding a doxycycline-regulated transactivator or CRISPR/Cas based variant (e.g., SpCas9 or Cpf1) for DNA cleavage, gene activation (Crispra), or gene repression (Crispri) when paired with an sgRNA.

In various embodiments, the promoter-less donor vectors described above and below further comprises a gene encoding one or more spaghetti monster fluorescent proteins (SM_FPs). In various embodiments, the one or more SM_FPs are each different SM_FPs. In various embodiments, the one or more SM_FPs are four different SM_FPs.

In various embodiments, the promoter-less donor vector further comprises a gene encoding one or more epitope tags. For example, 2, 3, 4, 5, 6, 7 8, 9, 10, 11, 12, 13, 14, or 15 epitope tags. The epitope tags may be the repeats or different tags. In various embodiments, the epitope tag is an HA tag, Myc tag, V5 tag, or Flag tag.

In various embodiments, the promoter-less donor vector comprises a large-cargo bacterial artificial chromosomes (BAC).

Animal Models

Various embodiments of the present invention provide for a non-human animal model and methods of generating the non-human animal model. The animal model can be used to model cancer driver mutations (e.g., gain of function oncogenes).

In various embodiments, generating the non-human animal model comprises providing a system for dual recombinase-mediated cassette exchange; administering the system for dual recombinase-mediated cassette exchange to the non-human animal, and subjecting the non-human animal to electroporation.

The system for dual recombinase-mediated cassette exchange provided and used to generate the non-human animal model is a system for dual recombinase-mediated cassette exchange of present invention as described herein.

In various embodiments, the method further comprises administering hypBase and/or reporter plasmids.

The system for dual recombinase-mediated cassette exchange electroporation can be administered to a location wherein testing is desired. For example, experiments to study the brain, the system can be injected into the lateral ventricle and electroporation can be conducted at that location. In another example, for experiments to study the spinal cord, the system can be injected, for example, into the cerebral spinal fluid, or into or near the spinal cord, and electroporation can done at or near the spinal cord.

In various embodiments, the non-human animal model comprises a system for dual recombinase-mediated cassette exchange as disclosed herein, wherein the dual Recombinase-Mediated Cassette Exchange has occurred.

In various embodiments, the non-human animal is a mouse. In other embodiments, the non-human animal is a rat, hamster, gerbil, pig, guinea pig, rabbit, monkey (e.g., rhesus monkey), baboon, chimpanzee, sheep, or dog. In various embodiments, the non-human animal is a genetically engineered mouse. In various embodiments, the non-human animal is a genetically engineered mouse with paired dual recombinase sites. In various embodiments, the mouse is a Rosa26mTmG (mTmG), Ai14, R26-CAG-LF-mTFP1, or IKMC mouse or mouse with similar paired dual recombinase sites.

Drug Screening

Various embodiments of the present invention provide for a method of screening a drug candidate, comprising: providing a non-human animal model of the present invention, administering the drug candidate, and assessing the effects of the drug candidate on the non-human animal model.

In various embodiments, the method further comprises selecting the drug candidate as a drug when the drug candidate provides a beneficial result to the non-human animal model. In various embodiments, the method further comprises validating the drug candidate as a drug when the drug candidate provides a beneficial result to the non-human animal model.

"Beneficial result" may include, but are in no way limited to, lessening or alleviating the severity of the disease condition, preventing the disease condition from worsening, curing the disease condition and prolonging a patient's life or life expectancy.

Methods of Treatment

Various embodiments of the present invention provide a method of treating a disease or condition in a subject, comprising: providing a cell comprising a system for dual recombinase-mediated cassette exchange of the present invention and administering the cell to the subject.

In various embodiments, the cell is a stem cell.

In various embodiments, dual Recombinase-Mediated Cassette Exchange has occurred in the cell.

Administering the cell to the subject can be performed by a route of administration that is appropriate for the disease condition. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

In various embodiments, the cell is administered by transplantation. Treatments include using transplanted cells with the dRMCE event to deliver growth factors, exosomal, or peptide therapies in diseases such as cancer, neurodegenerative disease, stroke, or epilepsy.

In various embodiments, the cell is transplanted and then subsequently targeted for dRMCE by electroporation or viral transduction.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Cloning

Flp-Cre constructs were generously provided by Y. Voziyanov and previously validated in the context of dRMCE. Our donor plasmids were derived from PGKneotpAlox2, using In-Fusion technique (Clontech) in combination with standard restriction digestion techniques. FRT site was created by annealing two oligos and infusing the insert into PGKneotpAlox2. Downstream generation of other donor plasmids were done by removing the existing ORF and adding a new cassette using In-Fusion or ligation. PB-CAG-plasmids were previously described.

Mice and Electroporation

Gt(ROSA)26Sortm4(ACTB-tdTomato, -EGFP)Luo/J mice were purchased from the Jackson Laboratory. mTmG were bred with wildtype CD1 mice (Charles River) to generate heterozygous mice. All mice were used in accordance with the Cedars-Sinai Institutional Animal Care and Use Committee. Postnatal lateral ventricle EPs were performed as previously described. P1-3 pups were placed on ice for ~5 min. All DNA mixtures contained 0.5-1 µg/µl of Flp-Cre expression vector, donor plasmid, hypBase, or CAG-reporter plasmids diluted in Tris-EDTA buffer unless noted otherwise. Fast green dye was added (10% v/v) to the mixture, which was injected into the lateral ventricle. Platinum Tweezertrodes delivered 5 pulses of 120 V (50 ms; separated by 950 ms) from the ECM 830 System (Harvard Apparatus). SignaGel was applied to increase conductance. Mice were warmed under a heat lamp and returned to their cages.

Tissue Preparation

After anesthesia, mouse brains were isolated and fixed in 4% PFA overnight at 4° C. Brains were embedded in 4% low melting point agarose and sectioned at 70 µm on a vibratome (Leica).

Immunohistochemistry

Immunohistochemistry was performed using standard methodology as previously described. All secondary antibodies (Jackson ImmunoResearch) were used at 1:500. Details on the primary antibodies can be found in Table 3.

TABLE 3

Antibodies used in the study

| | | |
|---|---|---|
| Abcam 13970 | Chicken anti-EGFP | 1:5000 |
| Abcam 95038 | Goat anti-V5 | 1:1000 |
| Active Motif | rb anti-H3f3a pS31 | 1:500 |
| Aves | Chicken anti-Myc | 1:500 |
| BD Pharmingen | Rat anti-PDGFRα | 1:500 |
| BD Pharmingen | Rt anti-Pecam1 | 1:250 |
| Calbiochem | Sheep anti-p53 | 1:1000 |
| Cell Signaling | rb anti-H3K27Me | 1:1000 |
| Cell Signaling | rb anti-Pdgfrb | 1:500 |
| Cell Signaling | rb anti-des | 1:500 |
| Cell Signaling 3724 | Rabbit anti-HA | 1:2000 |
| Cell Signaling 9308 | Rabbit anti-pRb1 | 1:500 |
| Clontech 9G9 | Mouse anti-tetR | 1:1000 |
| Clontech 9G9 | rb anti-dsred | 1:1000 |
| Dawen Cai (Univ of Mich) | Rabbit anti-dsRed | 1:1000 |
| Dawen Cai (Univ of Mich) | Guinea pig anti-mKate2 | 1:500 |
| Invitrogen 46-0705 | Mouse anti-V5 | 1:1000 |
| Kerafast | rat anti-tdtomato | 1:2000 |
| R&D Systems | Sheep anti-Dll1 | 1:500 |
| R&D Systems | Gt anti-Olig2 | 1:500 |
| Revmab | rb anti-H3f3a | 1:100 |
| Sigma | Mouse anti-Flag | 1:2500 |

Cell Culture and Nucleofection

Three heterozygous P0 mTmG pup brains were dissociated to establish the mouse neural stem cell line used in the study. The cell line was maintained as previously described. Cells were grown in media containing Neurobasal®-A Medium (Life Technologies 10888-022) supplemented with B-27 without vitamin A (Life Technologies 12587-010), GlutaMAX (Life Technologies 35050), Antibiotic-Antimycotic (Life Technologies 15240), hEGFP (Sigma E9644), heparin (Sigma H3393), and bFGF (Millipore GF003). Neural stem cell nucleofection was performed using the Nucleofector 2b device and Mouse Neural Stem Cell Kit according to manufacturer's recommendations (Lonza AG). The nucleofection mixture contained plasmids with equal concentrations of 10 ng/µl.

Imaging and Processing

All fixed images were collected on a Nikon AIR inverted laser confocal microscope. The live image of mNSCs was obtained on an EVOS digital fluorescence inverted microscope. For whole brain images, the automated stitching function of Nikon Elements was used. ND2 files were then imported into ImageJ to create Z-projection images, which were subsequently edited in Adobe Photoshop CS6. Adobe Illustrator CS6 was used for the final figure production.

Flow Cytometry

Cells were collected as previously described. Cells were briefly rinsed in PBS, removed by enzymatic dissociation suing Accutase (Millipore), pelleted at 250 g for 3 min, and resuspended in the media. FACS was done on a Beckman Coulter MoFlo at the Cedars-Sinai Flow Cytometry.

Western Blot

The cell pellets were re-suspended in Laemmli buffer and boiled for 5 min at 95° C. Protein concentrations were measured on a ThermoScientific NanoDrop 2000. After SDS-PAGE separation and transfer onto nitrocellulose membranes, proteins were detected using the antibodies listed on Table 3, diluted in 5% milk in 0.1% PBS-Tween. All secondary antibodies (Li-cor IRDye®) were used at 1:15000. Infrared detection was accomplished by the Li-Cor Odyssey® CLX Imaging System.

Doxycycline and Puromycin Administration

Doxycycline (Clontech 631311) was added to culture media at the final concentration of 100 ng/ml. Puromycin (Clontech 631305) was used at 1 μg/ml.

Multi-miR-E Knockdown Efficiency Quantification

We have previously used FlEx-based transgene expression, specifically Cre-mediated inversion and activation of EGFP cassette (FlEx-EGFP). To test our multi-miR-E targeting Nf1, Pten, and Trp53, we made a CAG-driven FlEx-based construct harboring the multiple miR-Es (FlEx-multi-miR-E). Postnatal mNSC line was established by dissociating CD1 pup brains, transfected with EGFP or FlEx-multi-miR-E and Cre-recombinase vector. Fluorescent cells were sorted and subjected to mRNA extraction and SYBR-based Fluidigm BioMark dynamic array using qPCR probes for Nf1, Pten, and Trp53.

Quantification of In Vivo MADR Efficiency

For each condition, two pups were electroporated with pCAG-TagBFP2-nls, pDonor-smFP-HA, and Flp-2A-Cre. The brains were taken two days post-EP, and two non-adjacent sections from each brain were stained with HA-Tag antibody and EGFP. For each section, ~25 BFP+ cells were randomly selected, among which HA+ and EGFP+ cells among BFP+ cells were counted. The proportions were averaged over four sections for each group.

PCR-Generation of U6-sgRNA Fragments

A short reverse primer and an ultramer forward primer (IDT DNA) were combined in a PCR reaction and subsequent purification to make concentrated sgRNAs (Ran et al., 2013). 100 ng of each fragment was combined with plasmid DNA for EP.

Sequencing InDel Mutations in Murine Tumor Cells

A pure population of tumor cells was obtained by FACS and genomic DNA was isolated (Qiagen DNeasy). Using primers flanking the gRNA target site, we PCR amplified the regions expected to contain InDel mutations for NF1, Trp53, and Pten. The PCR amplified fragments were topo cloned using the Thermo Fisher Zero Blunt TOPO kit and transformed into One Shot MAX Efficiency DH5-T1R cells.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A system, comprising:
   a promoter-less donor vector, comprising
   four polyadenylation signals (pAs) upstream from a transgene or a polynucleotide encoding an RNA,
   the transgene or the polynucleotide encoding the RNA, wherein the transgene or the polynucleotide encoding RNA comprises a disease associated mutation, and
   paired recombinase recognition sites selected from loxP, flippase recognition target (FRT), Vlox and its derivatives, Slox and its derivatives, Rox and its derivatives, or attb, wherein the transgene or polynucleotide encoding the RNA is in between the paired recombinase recognition sites; and
   one expression vector, comprising two genes encoding recombinases specific to the paired recombinase recognition sites, or
   two expression vectors, the first expression vector comprising one gene encoding a first recombinase that is specific to one of the paired recombinase recognition sites, and the second expression vector comprising one gene encoding a second recombinase that is specific to the other of the paired recombinase recognition sites.

2. The system of claim 1, wherein the promoter-less donor vector further comprises a post-transcriptional regulatory element.

3. The system of claim 1, wherein the promoter-less donor vector further comprises a polyadenylation signal downstream from the transgene or the polynucleotide encoding the RNA.

4. The system of claim 1, wherein the promoter-less donor vector comprising the four pAs comprise a PGK polyadenylation signal (pA) and trimerized SV40 pA upstream from the transgene or the polynucleotide encoding the RNA; and wherein the paired recombinase recognition sites are lox P and flippase recognition target (FRT) and the transgene or polynucleotide encoding the RNA is in between the loxP and flippase recognition target (FRT); and wherein the promoter-less donor vector comprises a rabbit beta-globin pA; and a woodchuck hepatitis virus post-transcriptional regulatory element (WPRE).

5. The system of claim 1, wherein the paired recombinase recognition sites are loxP and flippase recognition target (FRT), and the recombinases are cre and flp.

6. The system of claim 1, wherein the RNA is siRNA.

7. The system of claim 1, wherein the RNA is shRNA.

8. The system of claim 1, wherein the RNA is sgRNA.

9. A promoter-less donor vector, comprising:

four polyadenylation signals (pAs) upstream from a transgene or a polynucleotide encoding an RNA, wherein the transgene or the polynucleotide encoding RNA comprises a disease associated mutation;

the transgene or the polynucleotide encoding the RNA in between paired recombinase recognition sites selected from loxP, flippase recognition target (FRT), Vlox and its derivatives, Slox and its derivatives, Rox and its derivatives, or attb.

10. The promoter-less donor vector of claim 9, further comprising a post-transcriptional regulatory element.

11. The promoter-less donor vector of claim 9, further comprising a polyadenylation signal downstream from the transgene or the polynucleotide encoding the RNA.

12. The promoter-less donor vector of claim 9, wherein the four polyadenylation signals comprise a PGK polyadenylation signal (pA) and trimerized SV40 pA upstream from the transgene or RNA; and wherein the paired recombinase recognition sites are lox P and flippase recognition target (FRT) and the transgene or polynucleotide encoding the RNA is in between loxP and flippase recognition target (FRT); and wherein the promoter-less donor vector comprises:

a rabbit beta-globin pA; and a woodchuck hepatitis virus post-transcriptional regulatory element (WPRE).

* * * * *